United States Patent
Veronese et al.

(10) Patent No.: US 6,528,485 B1
(45) Date of Patent: Mar. 4, 2003

(54) SITE-SPECIFIC PREPARATION OF POLYETHYLENE GLYCOL-GRF CONJUGATES

(75) Inventors: Francesco Maria Veronese, Padova (IT); Paolo Caliceti, Padova (IT); Oddone Schiavon, Padova (IT)

(73) Assignee: Applied Research Systems ARS Holding N.V., Curacao (AN)

( * ) Notice: Subject to any disclaimer, the term of this patent is extended or adjusted under 35 U.S.C. 154(b) by 0 days.

(21) Appl. No.: 09/587,460

(22) Filed: Jun. 5, 2000

Related U.S. Application Data

(63) Continuation of application No. PCT/EP98/07748, filed on Dec. 1, 1998.

(30) Foreign Application Priority Data

Dec. 3, 1997 (EP) .............................. 97121264

(51) Int. Cl.[7] ........................ A61K 38/25; A61K 47/48; C07K 17/08; C12N 11/08
(52) U.S. Cl. .............................. 514/12; 514/12; 514/2; 530/399; 530/345; 530/344; 530/338; 530/334; 530/324; 530/406; 530/410; 424/198.1
(58) Field of Search ..................... 424/198.1; 514/12, 514/2; 530/399, 334, 345, 324, 338, 344, 406, 410

(56) References Cited

U.S. PATENT DOCUMENTS 5,183,660 A * 2/1993 Ikeda et al. ................. 424/94.3

OTHER PUBLICATIONS

A. Abuchowski, et al., Alteration of Immunological Properties of Bovine Serum Albumin by Covalent Attachment of Polyethylene Glycol, J. Biol. Chem., 1977a vol. 252, pp. 3578–3581.

A. Abuchowski, et al., Effect of Covalent Attachment of Polyethylene Glycol on Immunogenicity and circulating Life of Bovine Liver Catalase, J. Biol. Chem., vol. 252 19776, pp. 3582–3586.

C.O. Beauchamp et al., A New Procedure for the Synthesis of Polyethylene Glycol–Protein Adducts; Effects on Function, Receptor Recognition, and Clearance of Superoxide Dismutase, Lactoferrin, and $\alpha_2$–Macroglobulin, Anal, Biochem., vol. 131, 1983, pp. 25–33.

P. Caliceti, et al., Active Site Protection of Proteolytic Enzymes by Poly(ethylene glycol) Surface Modification, J. Bioactive Compatible Polymer, 8, 1993, pp. 41–50.

R.M. Campbell, et al., Pegylated peptides V, J. Peptide Res., 49, 1997, pp. 527–537.

W. C. Chan, et al., A Novel 4–Minobenzyl Ester–based Carboxy–protecting Group for Synthesis of Atypical Peptides by Fmoc–Bu[t] Solid–phase Chemistry, J. Chem., Soc. Chem., Commun., 1995, pp. 2209–2210.

R. Clark, et al., Long–acting Growth Hormones Produced by Conjugation with Polyethylene Glycol., J. Biol. Chem., 36, 1996, pp. 21969–21977.

C. Delgado, et al., Coupling of Poly(ethylene glyco) to Albumin under Very Mild Conditions by Activation with Tresyl Chloride: characterization of the Conjugate by Partitioning in Aqueous Two–Phase Systems, Biotechnoogy and Applid Biochemistry 12, pp. 119–128, 1990.

D. Bourgin, et al., Unexpected Side–Product Formation During the Coupling of an α–Hydroxy Acid to An amino Acid Ester with TBTU, Peptides 1996, Proceedings of the $24^{24}$ European Peptide Symposium, Edinburgh, Scotland, 1997 abstract only.

A.M. Felix, et al., Pegylated peptides IV, Int. J. Peptide Protein Res., 46, 1995, pp. 253–264.

T.M. Fisch, et al., Multiple sequence elements in the c–fos promoter mediate induction by cAMP, Genes and Development, 3, 1989, pp. 198–211.

T.W. Greene, et al., Protective Groups in Organic Synthesis, John Wiley and Sons Inc. Pub. 1991, pp. 331–333.

A.S.F.A. Habeed, Determination of Free Amino Groups in Proteins by Trinitrobenzenesulfonic Acid, Anal. Bioche., 14, 1966, pp. 328–336.

J.M. Harris, Laboratory Synthesis of Polyethylene Glycol Derivatives, Rev. Mcromol. Chem. Phys. C5, 1985, pp. 325–373.

S.J. Hocart, et al., Effect of Reductive Alkylation of D–Lysine in Position 6 on the Histamine–Releasing Activity of Luteinizing Hormone–Releasing Hormone Antagonists, J. Med. Chem., 30(4), 1987, pp. 739–743.

Y. Lu, et al., Pegylated peptides II, Int. J. Peptide Protein Res., 43, 1994, pp. 127–138.

C. Monfardini, et al., A Branched Monomethoxypoly(ethylene glycol) for Protein Modification (Biocon. Chem. 6., 1995, pp. 62–69.

M. Morpurgo et al., Preparation and Characterization of Poly(ethylene glycol) Vinyl Sulfone, Biocon Chem., 7, pp. 1996, p. 363–368.

W.A. Murphy, et al., Potent Long–Acting Alkylated Anallogs of GrowthHormone–Releasing Factor, Peptide Research, 1(1), 1988, pp. 36–41.

C.S. Pande, et al., Camphorquinone–10–sulfonic acid and derivatives: Convenient reagents for reversible modification of arginine residues, Proc. Natl. Acad. Sci. USA 77, 1980, pp. 895–899.

L. Sartore, et al., Enzyme Modification by MPEG with an Amino Acid or peptide as Spacer Arms, Appl. biocem. Biotechnol., 27, 1991, pp. 45–54.

(List continued on next page.)

*Primary Examiner*—Karen Cochrane Carlson
*Assistant Examiner*—Chin-Min Kam
(74) *Attorney, Agent, or Firm*—Browdy and Neimark, PLLC

(57) ABSTRACT

Described are various human growth hormone releasing factor-PEG conjugates as well as their pharmaceutical use.

9 Claims, 14 Drawing Sheets

OTHER PUBLICATIONS

L. Sartore, et al., Accurate Evaluation Method of the Polymer Content in Monomethoxy(Polyethylene Glycol) Modified Proteins Based on Amino Acid Analysis Applied Biochem. Biotechnol., 31, 1991, pp. 213–222.

G.E.C. Sims, et al., A Method for the Estimation of Polyethylene Glycol in Plasma Protein Fractions, Anal. Biochem. Biotechnol., 31, 1980, pp. 60–63.

James P. Tam, et al., Strong Acid Deprotection of Synthetic Peptides: Mechanisms and Methods, The Peptides, Academic Press Inc., 9, 1987 pp. 185–249.

F.M. Veronese, et al., Surface Modification of Proteins, Appl. Biochem, 11, 1985, pp. 141–152.

K. Miyata, et al., Altered Properties of Serratia Superoxide Dismutase by Chemical Modification, Agric. Biol. Chem, 52, 1988, pp. 1575–1581.

S. Zalipsky, et al., Succinimidyl Carbonates of Polyethylene Glycol, American Chemical Society, 1991, Chapter 10, pp. 91–100.

S. Zalipsky, et al., Attachment of Drugs to Polyethylene Glycols., Europ. Polym. J., 19, #12, 1983, pp. 1177–1183.

* cited by examiner

NH2-Tyr-Ala-Asp-Ala-Ile-Phe-Thr-Asn-Ser-Tyr-Arg- Lys-Val-Leu-Gly-Gln-Leu-Ser-Ala-Arg- Lys-Leu-Leu-Gln-Asp-Ile-Met-Ser-Arg-NH2
1 10 20

Fig. 1

SITE-SPECIFIC PREPARATION OF POLYETHYLENE GLYCOL-GRF CONJUGATES

CROSS REFERENCE TO RELATED APPLICATIONS

This is a continuation application of International Application PCT/EP98/07748, with an International filing date of Dec. 1, 1998.

FIELD OF THE INVENTION

The present invention relates to a method for the site-specific preparation of hGRF-PEG conjugates containing one or more than one PEG units (per hGRF) covalently bound to $Lys^{12}$ and/or $Lys^{21}$ and/or $N^\alpha$, characterized in that the conjugation reaction between the hGRF peptide and activated PEG is carried out in solution and the desired hGRF-PEG conjugate is purified by chromatographic methods.

The conjugates prepared by this method, as well as their use in the treatment, prevention or diagnosis of growth-hormone related disorders, are also an object of the present invention.

BACKGROUND OF THE INVENTION

In the early 1980's several groups isolated and characterized growth hormone releasing factor (GRF).

GRF (also called Somatorelin) is a peptide secreted by the hypothalamus which acts on its receptor and can promote the release of growth hormone (GH) from the anterior pituitary. It exists as 44-, 40-, or 37-amino acid peptide. the 44-amino acids form may be converted physiologically into shorter forms. All three forms are reported to be active, the activity residing mainly in the first 29 amino acid residues. A synthetic peptide corresponding to the 1-29 amino acid sequence of human GRF [hGRF(1-29)], also called Sermorelin, has been prepared by recombinant DNA technology as described in European Patent EP 105 759.

Sermorelin has been used in the form of acetate for the diagnosis and treatment of growth hormone deficiency.

GRF has indeed a therapeutic value for the treatment of certain growth-hormone related disorders. The use of GRF to stimulate the release of GH is a physiological method in promoting long, bone growth or protein anabolism.

One problem associated with the use of GRF relates to its short biological half-life (about 12 to 30 minutes). The hGRF(1-29)-$NH_2$ is subject to enzymatic degradation and is rapidly degraded in the plasma via dipeptidylpeptidase IV (DPP-IV) cleavage between residues $Ala^2$ and $Asp^3$.

It is therefore advantageous to develop biologically stable, long-acting GRF analogues using specific chemical modification of GRF, in order to prevent or slow down enzymatic degradation.

Polyethylene glycol (PEG) is a hydrophilic, biocompatible and non-toxic polymer of general formula $H(OCH_2CH_2)_nOH$, wherein $n \geq 4$. Its molecular weight could vary from 200 to 20,000 daltons.

It has been demonstrated that the chemical conjugation of PEG in its mono-methoxylated form to proteins and/or peptides significantly increases their duration of biological action. Like carbohydrate moieties in a glycoprotein, PEG provides a protective coating and increases the size of the molecule, thus reducing its metabolic degradation and its renal clearance rate PEG conjugation is an already established methodology for peptide and protein delivery pioneered by the fundamental studies of Davis and Abuchowski (Abuchowski et al., 1977a and 1977b). PEG conjugation to peptides or proteins generally resulted in non-specific chemical attachment of PEG to more than one amino acid residue. One of the key issues with this technology is therefore finding appropriate chemical methods to covalently conjugate PEG molecule(s) to specific amino acid residues.

For example, the trichlorotriazine-activated PEG, which was found to be toxic and reacted in a non-specific way, was later on replaced by various PEG reagents with chemical linkers that could react specifically to amino groups (Benchamp et al., 1983; Veronese et al., 1985; Zalipsky et al., 1983; Zalipski et al., 1990; and Delgado et al., 1990), to sulphydryl groups (Sartore et al., 1991; and Morpurgo et al., 1996) or to guanidino residues (Pande et al., 1980).

Various PEG-protein conjugates were found to be protected from proteolysis and/or to have a reduced immunogenicity (Monfardini et al., 1995; and Yamsuki et al., 1988).

Another technical difficulty in protein pegylation arises from the fact that PEG-protein conjugates usually have various number of PEG molecules attached and result in a mixture of conjugates with different PEG:protein stoichiometries. Site-specific pegylation remains a chemical challenges The conjugation of PEG to GH represents a typical example of such problem (Clark et al., 1996). It was demonstrated that Lys-residues of GH were pegylated at random positions.

To avoid or reduce the loss of enzyme activity, the active site could be protected in advance, thus allowing enzyme pegylation to occur at non-active site(s) (Caliceti et al., 1993).

Another approach was recently proposed for the site-specific conjugation of PEG to low molecular weight peptides, such as GRF. which was prepared by solid-phase peptide synthesis. In these conjugates a pegylated amino acid, prepared in advance, was introduced into the peptide sequence during the solid-phase synthesis. This procedure, however, dramatically complicates product purification that is known to be the critical step in solid phase synthesis. The presence of PEG, for its high molecular weight and its polydispersivity, is likely to yield final products with unacceptable impurities and/or products with missing amino acids, the latter being considered to occur commonly in the Merrifield procedure.

Mono-pegylation, meaning that only one PEG molecule is attached, using solid-phase synthesis to specific amino acid residues of $(Ala^{15})$-hGRF(1-29)-$NH_2$ has been recently reported in the literature (Felix et al., 1995). This study shows that $(Ala^{15})$-hGRF(1-29)-$NH_2$ pegylated at residues 21 or 25 retains the full in-vitro potency of the parent $(Ala^{15})$-hGRF(1-29)-$NH_2$. There is however no in7-vivo data to show whether these pegylated conjugates exhibit a longer duration of action with respect to the non-pegylated counterpart.

More recently, it has been demonstrated (Campbell et al., 1997) that the attachment of PEG with different molecular weights to the C-terminus of several analogs of hGRF, again using solid-phase synthesis, had enhanced duration of action in both pig and mouse models as compared to the non-pegylated counterpart.

DESCRIPTION OF THE INVENTION

In contrast to the solid-phase preparation of mono-pegylated hGRF mentioned above, the present invention relates to site-specific pegylation of hGRF in solution phase.

hGRF was found to have a low solubility in a neutral/alkaline buffer solution, a chemical condition whereby most efficient pegylation reaction occurs. In a diluted hGRF solution, the hydrolysis of the activated PEG (such as the PEG ester) tends to decrease the yield of the pegylation reaction.

It was discovered by the Applicant that, in a suitable solvent whereby hGRF has a high solubility, it is possible to carry out a site-specific pegylation reaction in solution phase. In this way, even if the starting hGRF peptide is non-protected, the PEG chains will bind with high yields and almost exclusively to the primary amino groups ($\epsilon$-amino groups) of $Lys^{12}$, $Lys^{21}$ and/or $N^{\alpha}$. depending upon the reaction conditions. The following four conjugates, which are also covered by the present invention, were obtained, the hGRF:PEG stoichiometric ratio in the conjugates mainly depending on the molar ratio of PEG to hGRF:

hGRF-PEG conjugate, in which 1 PEG molecule is covalently bound to $Lys^{12}$, hGRF-PEG conjugate, in which 1 PEG molecule is covalently bound to $Lys_{21}$, hGRF-2PEG conjugate, in which 2 PEG molecules are covalently bound to both $Lys^{12}$ and $Lys^{21}$; and hGRF-3PEG conjugate, in which 3 PEG molecules are covalently bound to both $Lys^{12}$ and $Lys^{21}$ and also to $N^{\alpha}$.

"$N^{\alpha}$" through out the present invention means the amino group at the N-terminal position of the peptide (Tyr).

Further to this step, it is possible to carry out a simple chromatographic fractionation of the conjugates obtained in the reaction either by gel filtration or by direct application to a C18 HPLC column eluted by water/acetonitrile gradient. The second method is preferred, since large scale preparation and purification of the products could be obtained.

Therefore, the main embodiment of the present invention is a method for the site-specific preparation of different hGRF-PEG conjugates containing one or more than one PEG units (per hGRF) covalently bound to $Lys^{12}$ and/or $Lys^{21}$ and/or $N^{\alpha}$, characterized in that the pegylation reaction is carried out in solution and the desired hGRF-PEG conjugate is purified, for example, by chromatographic methods.

hGRF-PEG conjugates containing one or more PEG units (per mole of hGRF) covalently bound to $Lys^{12}$ and/or $Lys^{21}$ and/or $N^{\alpha}$ are also covered by the present invention. The hGRF-PEG conjugates, in which 1 PEG molecule is covalently bound to $Lys^{12}$ or to $Lys^{21}$, are the preferred products of the present invention.

According to another embodiment of the present invention, if one or more of these three amino groups to which PEG chains bind, are reversibly protected by certain chemical groups from pegylation, the pegylation reaction will give directly the desired conjugate with specific pegylation sites, which can then be isolated from the reaction mixture, for example, by ultrafiltration or other chromatographic methods. In this case, the preparation method can further, optionally, comprise a de-protection reaction.

The de-protection reaction is preferably carried out according to known methods and depending on the chemical protective group to be removed.

According to this invention the term "hGRF", unless otherwise specified, is intended to cover any human GRF peptides, with particular reference to the 1-44, 1-40. 1-29 peptides and the corresponding amides thereof (containing an amide group at the N-terminus or C-terminus). The preferred hGRF peptide is hGRF(1-29)-$NH_2$ whose amino acid sequence is reported in SEQ ID NO:1.

The "activated PEG" (or "pegylating agent") is any PEG derivative, which can be used as protein modifier, because it contains a functional group capable of reacting with some functional croup in the protein/peptide to produce the PEG-protein/peptide conjugates. A review of PEG derivatives useful as protein modifiers can be found in Harris (1985). The activated PEG can be an alkylating reagent, such as PEG aldehyde, PEG epoxide or PEG tresylate, or it can be an acylating reagent, such as PEG ester.

The activated PEG is preferably used in its mono-methoxylated form. It has preferably a molecular weight between 2,000 and 20,000. Mono-methoxylated $PEG_{5,000}$ is particularly preferred for the preparation of the activated PEG according to the present invention.

If activated PEG is an acylating agent, it preferably contains either a norleucine or ornithine residue bound to the PEG moiety via an amide linkage. These residues allow a precise determination of the linked PEG units per mole of peptide (see for example Sartore et al., 1991). Therefore, more in particular, the preferred activated PEG is mono-methoxylated $PEG_{5,000}$ linked by means of an amide bond to the alpha amino group of norleucine, that is activated at the carboxy group as succinimidyl ester.

Branched PEGs are also in common use. The branched PEGs can be represented as $R(-PEG-OH)_m$ in which R represents a central core moiety such as pentaerythritol or glycerol, and m represents the number of branching arms. The number of branching arms (m) can range from three to a hundred or more. The hydroxyl groups are subject to chemical modification.

Another branched form, such as that described in PCT patent application WO 96/21469, has a single terminus that is subject to chemical modification. This type of PEG can be represented as $(CH_3O-PEG-)_pR-X$, whereby p equals 2 or 3. R represents a central core such as lysine or glycerol, and X represents a functional group such as carboxyl that is subject to chemical activation. Yet another branched form, the "pendant PEG", has reactive groups, such as carboxyl, along the PEG backbone rather than at the end of PEG chains.

All these branched PEGs can be "activated" as indicated above.

"Chromatographic methods" means any technique that is used to separate the components of a mixture by their application on a support (stationary phase) through which a solvent (mobile phase) flows. The separation principles of the chromatography are based on the different physical nature of stationary and mobile phase.

Some particular types of chromatographic methods, which are well-known in the literature, include: liquid, high pressure liquid, ion exchange, absorption, affinity, partition, hydrophobic, reversed phase, gel filtration, ultrafiltration or thin-layer chromatography.

"Pegylation" is the reaction by which a PEG-protein/peptide conjugate is obtained starting from the activated PEG and the corresponding protein/peptide.

The molar ratio PEG:hGRF can be 1:1, 2:1 or 3:1, depending on which conjugate is sought at high yields.

The solvent of the pegylation reaction is selected from the group consisting of a highly concentrated nicotinamide aqueous solution. a buffered aqueous solution of a defolding agent (such as urea) or a polar organic solvent selected among dimethyl sulfoxide, dimethyl formamide/buffer or acetonitrile/buffer.

The pH of the solution is usually kept between 7 and 9.

A non-limitative list of protective chemical groups for $Lys^{12}$ and $Lys^{21}$ includes: Alloc (allyloxycarbonyl), Dde (1-(4,4-Dimethyl-2,6-dioxocyclohex-1-ylidene)ethyl), Adpoc (1-(1'-Adamantyl)-1-methyl-ethoxycarbonyl) or 2-Cl-Z (2-Chlorobenzyloxycarbonyl). Alloc is the preferred protective group for the lysine group.

After pegylation Alloc can be removed according to one of the methods described in Greene T. W. et al., 1991). Dde can be removed with 2% hydrazine in DMF (see W. C. Chan et al., 1995). Adpoc can be removed similarly to Alloc (see also D. Bourgin et al., 1997). 2-Cl-Z can be requires a stronger acid deprotection (HF, TFMSA, HBr) or hydrogenation (see also Tam et al., 1987).

The protective groups for $N^\alpha$ can be an alkyl group. such as methyl, ethyl, propyl, isopropyl, butyl, t-butyl, benzyl or cyclohexyl. Isopropyl is the preferred one. These alkyl groups can be introduced by reductive alkylation (see Murphy et al., 1988 or Hocart et al., 1987).

($N^\alpha$-isopropyl-Tyr$^1$,Lys(Alloc)$^{12}$)-hGRF and (Lys(Alloc)$^{12,21}$)-hGRF are also covered by the present invention, as useful and new intermediates of the pegylation reaction.

It has also been discovered that the pegylation of the present invention:
1. does not modify the conformation of the peptide,
2. increases the resistance to the proteolytic degradation,
3. does not affect, or only slightly decreases, the biological activity, depending upon the extent of pegylation and
4. allows to obtain products (the conjugates), which are more soluble in aqueous buffered solutions.

Another object of the present invention is to provide the hGRF-PEG conjugates in substantially purified form in order for them to be suitable for use in pharmaceutical compositions as active ingredients.

In a further aspect, the present invention provides the use of the conjugates of the invention in the manufacture of a medicament for treatment, prevention or diagnosis of growth hormone-related disorders, such as for example growth hormone deficiency(GHD), in particular pediatric growth hormone deficiency.

The medicament is preferably presented in the form of a pharmaceutical composition comprising the conjugates of the invention together with one or more pharmaceutically acceptable carriers and/or excipients. Such pharmaceutical compositions form yet a further aspect of the present invention.

An embodiment of the invention is the administration of a pharmacologically active amount of the conjugates of the invention to subjects at risk of developing a growth hormone-related disease or to subjects already showing such pathology.

A further object of this invention is a method of treatment. prevention or diagnosis of growth hormone-related disorders, comprising administering an effective amount of the conjugates of the invenion, in the presence of one or more pharmaceutically acceptable excipients.

An "effective amount" refers to an amount of the active ingredients that is sufficient to affect the course and the severity of the disorders described above, leading to the reduction or remission of such pathology. The effective amount will depend on the route of administration and the condition of the patient.

"Pharmaceutically acceptable" is meant to encompass any carrier, which does not interfere with the effectiveness of the biological activity of the active ingredient and that is not toxic to the host to which is administered. For example, for parenteral administration, the above active ingredients may be formulated in unit dosage form for injection in vehicles such as saline, dextrose solution, serum albumin and Ringer's solution.

Besides the pharmaceutically acceptable carrier, the compositions of the invention can also comprise minor amounts of additives, such as stabilizers, excipients, buffers and preservatives.

Any route of administration compatible with the active principle can be used. The preferred is the parenteral administration, such as subcutaneous, intramuscular or intravenous injection. The dose of the active ingredient to be administered depends on the basis of the medical prescriptions according to age, weight and the individual response of the patient.

The dosage of the active ingredient for the human therapy can be between 5 and 6,000 $\mu$g/Kg body weight and the preferable dose is between 10 and 300 $\mu$g/Kg body weight.

The present invention has been described with reference to the specific embodiments, but the content of the description comprises all modifications and substitutions which can be brought by a person skilled in the art without extending beyond the meaning and purpose of the claims.

The invention will now be described by means of the following Examples, which should not be construed as in any way limiting the present invention. The Examples will refer to the Figures specified here below.

DESCRIPTION OF THE FIGURES

FIG. 1 shows the amino acid sequence of hGRF(1-29)-NH$_2$. Arrows indicate the possible site(s) of pegylation.

EXAMPLES

Abbreviations

Figure 2:
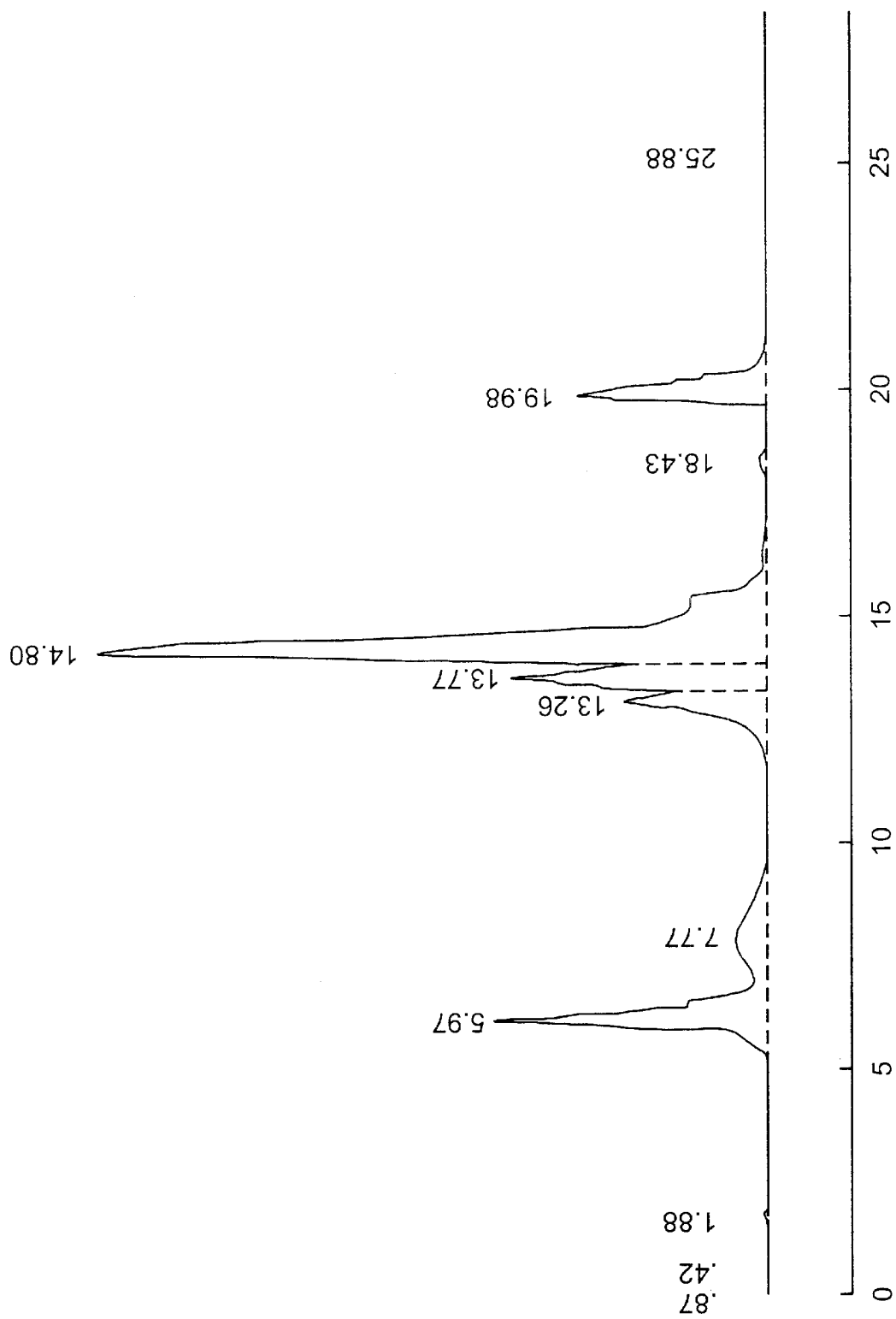
FIG. 2 shows the reversed-phase HPLC chromatography of the mixture obtained after the pegylation reaction in DMSO carried out as described in Example 1. The first two major peaks are the conjugates containing 1 PEG chain per mole of hGRF The following minor peak is the conjugate hGRF:2PEG and the last minor peak the conjugate hGRF:3PEG.

Acetonitrile (ACN), allyloxycarbonyl (Alloc), Benzyl (BZL), tert-Butyloxycarbonyl (Boc), Dichloromethane (DCM), Diisopropylethylamine (DIEA). Dimethyl Formamide (DMF), dimethyl sulphoxide (DMSO), 9-Fluorenylmethyloxycarbonyl (FMOC), 2-(1H-Benzotriazole-1-yl)-1,1,3,3-tetramethyluronium hexafluorophosphate (HBTU), 1-(hydroxybenzotriazole (HOBt,), methyl-t-butyl ether (MTBE), norleucine (Nle), N-methyl pyrrolidone (NMP), 2,2,5,7,8-Pentamethyl-chroman-6-sulfonyl (Pmc), tert-Butyl (tBu), Trifluoroacetic Acid (TFA), Triphenylmethyl (Trt).

EXAMPLE 1
Solution-phase Pegylation of hGRF

In these experiments mono-methoxylated $PEG_{5,000}$ ($MPEG_{5,000}$) linked by means of an amide bond to the alpha amino group of norleucine, that is activated at the carboxy group as succinimidyl ester, was used as pegylating reagent. It can be prepared for example as described in Lu et al., 1994.

Human $GRF_{1-29}$ hGRF(1-29)-$NH_2$ supplied by Bachem was used as hGRF peptide.

Given the low solubility of hGRF(1-29) in water solution at neutral or slightly alkaline pH needed for the pegylation, alternative reaction conditions A to E have been adopted:

A. Dimethyl sulphoxide: 20 mg of peptide were dissolved in 1 ml DMSO and proper amounts of pegylating reagent were added at once.
B. Dimethyl formamide/0.2 M borate buffer pH 8.0 in a volume ratio of 1:1: peptide and proper amounts pegylating reagent were added at once.
C. Highly concentrated nicotinamide aqueous solution (200 mg/ml): 200 mg of nicotinamide were added to a solution of 40 mg of hGRF(1-29) in 1 ml of 10 mM acetic acid. 1 ml of 0.2 M borate buffer at pH 8.0 was added to the acidic solution to reach the desired pH, before the addition of proper amounts of pegylating reagent.
D. Acetonitrile /0.2 M borate buffer pH 8.0 in a volume ratio of 1:1 and proper amounts of pegylating reagent were added at once.
E. 0.2 M borate buffer, 5 M urea, pH 8.0 and proper amounts of pegylating reagent were added at once.

The dry PEG reagent was added under stirring to reach final PEG:hGRF molar ratios of 1:1, 2:1 or 3:1. A 2:1 ratio is the preferred one.

The use of different PEG:hGRF molar ratios allowed the preparation of a reaction mixture with a predominant conjugate being the desired conjugate.

The reaction-solution was left standing for 5 hours at room temperature before purification.

The following 4 hGRF-PEG conjugates (A1-A4) are obtained:

A1: $(Lys(MPEG_{5,000}-CH_2-CO-Nle-CO)^{12}-hGRF(1-29)-NH_2)$,
A2: $(Lys(MPEG_{5,000}-CH_2-CO-Nle-CO)^{21}-hGRF(1-29)-NH_2)$,
A3: $(Lys(MPEG_{5,000}-CH_2-CO-Nle-CO)^{12,21}-hGRF(1-29)-NH_2)$ and
A4: $N^{\alpha}-(MPEG_{5,000}-CH_2-CO-Nle-CO)(Lys(MPEG_{5,000}-CH_2-CO-Nle-CO)^{12,21}-hGRF(1-29)-NH_2)$.

The excess of DMSO dimethyl formamide, acetonitrile or urea and the side-product of reaction (hydroxysuccinimide) were removed by gel ultrafiltration using a 1,000 D cut-off membrane. The volume was brought to 10 ml with 10 mM acetic acid and then reduced to 1 ml. The procedure was repeated three times.

The hGRF-PEG conjugates were isolated by gel filtration chromatography or alternatively by reversed-phase chromatography.

EXAMPLE 2
Gel Filtration Chromatography

By gel filtration chromatography the products were fractionated on the basis of the different molecular weight of the components (in this case, conjugates hGRF-PEG 1:1 MW=8,358, hGRF-PEG 1:2 MW=13,358, and hGRF-PEG 1:3 MW=18,358. Unconjugated hGRF MW=3358). The separation was performed by using a serial column system Superdex 75-Superose 12 resin (Biotech, Pharmacia) eluted with 10 ml acetic acid at a flow rate of 1.5 ml/min.

The collected fractions of 1 ml were analysed by OD at 280 nm for protein content and by iodine test for PEG content (Sims et al., 1980).

After pegylation in DMSO using a hGRF:PEG molar ratio of 1:1, three peaks were obtained:
a hGRF-PEG conjugate at an elution volume of 132 ml (major peak);
a hGRF-PEG conjugate at an elution volume of 108 ml (minor peak); and
unconjugated hGRF at an elution volume of 108 ml (minor peak).

After pegylation in DMSO using a hGRF:PEG molar ratio of 1:2, three peaks were obtained:
a hGRF-PEG conjugate at an elution volume of 108 ml (major peak);
a hGRF-PEG conjugate at an elution volume of 132 ml (minor peak); and
a hGRF-PEG conjugate at an elution volume of 73 ml (minor peak).

After pegylation in DMSO using a hGRF:PEG molar ratio of 1:3, two peaks were obtained:
a hGRF-PEG conjugate at an elution volume of 73 ml (major peak); and
a hGRF-PEG conjugate at an elution volume of 108 ml (minor peak).

The eluted peaks were collected, concentrated by ultrafiltration using a 1,000 D cut-off membrane, lyophilised, dissolved in 10 mM acetic acid and characterised as herein after reported for their identification and quantification.

The peak at the elution volume of 73 ml was found to correspond to compound A4.

The peak at the elution volume of 132 ml was found to correspond to compound A3.

The peak at the elution volume of 108 ml was found to correspond to a mixture of compounds A2 and A1.

The peak eluted at 232 ml was found to be unconjugated hGRF.

However, this method of purification does not allow to separate hGRF-PEG conjugates having the same molecular weight but different pegylation site (positional isomers).

EXAMPLE 3

Reversed-Phase Chromatography

A more specific fractionation was carried out by hydrophobic chromatography using an RP-HPLC C18 column. This procedure can separate eventual isomers having the same molecular weight. In fact, with this method the single peak corresponding to the conjugates with 1 PEG covalently bound obtained by gel filtration was found to split in two peaks.

The reversed-phase chromatography was carried out using a RP-HPLC C18 preparative column (Vydac) eluted with a gradient of $H_2O/0.05\%$ TFA (Eluent A) and acetonitrile/=0.05% TFA (Eluent B), as follows:

| 0–5 min. | 35% A |
|---|---|
| 5–35 min | 35% A → 2% A |
| 35–38 min | 2% A |
| 38–40 min | 2% A → 35% A. |

Flow rate: 10 ml/min; loop 1 μl; UV-Vis. Detector at 280 nm.

After pegylation in DMSO using a hGRF:PEG molar ratio of 1:1, 4 peaks were obtained:

| 1 | 13.2 min | major peak; |
|---|---|---|
| 2 | 13.7 min | major peak; |
| 3 | 14.4 min | minor peak; and |
| 4 | 8.9 min | minor peak. |

After pegylation in DMSO using a hGRF:PEG molar ratio of 1:2, 4 peaks were obtained:

| 1 | 13.2 min | minor peak; |
|---|---|---|
| 2 | 13.7 min | minor peak; |
| 3 | 14.4 min | major peak; and |
| 4 | 15.5 min | minor peak. |

After pegylation in DMSO using a hGRF:PEG molar ratio of 1:3, 2 peaks were obtained:

| 1 | 14.4 min | minor peak; and |
|---|---|---|
| 2 | 15.5 min | major peak. |

The eluted peaks were collected, evaporated to eliminate acetonitrile and TFA and then lyophilised. The dry product was dissolved in 10 mM acetic acid solution and analysed as reported herein after for identification and quantification of the isolated species.

The hGRF-PEG conjugate eluted at 13.2 min. was found to be compound A1 (GRF-1PEG, 1st peak).

The hGRF-PEG conjugate eluted at 13.7 min. was found to be compound A2 (GRF-1PEG, 2nd peak).

The hGRF-PEG conjugate eluted at 14.4 min. was found to be compound A3 (GRF-2PEG).

The hGRF-PEG conjugate eluted at 15.5 min. was found to be compound A4 (GRF-3PEG).

The peak eluted at 8.9 min. was found to be unconjugated hGRF. As a typical example, the reversed-phase chromatography of the pegylation products obtained using a 2:1 PEG:hGRF molar ratio is reported in FIG. 2.

The dry products were obtained by solvent evaporation/lyophilization.

EXAMPLE 3a

Solution-Phase Pegylation of hGRF, using $PEG_{10,000}$

In this example a branched monomethoxy PEG having a molecular weight of 10,000 Dalton with lysine as spacer (supplied by Shearwater Polymers, Inc.) was used. This branched PEG has been obtained by linking to each amino group of lysine a $PEG_{5,000}$.

The carboxy group of the spacer lysine, activated as succinimidyl ester, was reacted in DMSO to the amino groups of hGRF(1-29)-$NH_2$ using a molar ratio of 0.9 moles of PEG to 1 mole of GRF.

The solvent was removed and the residue fractionated by gel exclusion chromatography in a preparative column Superose 12 TM. Two peaks, corresponding to two hGRF-PEG conjugates were eluted. The first minor peak corresponded to the conjugate having two $PEG_{10,000}$ units bound to hGRF, the second major peak corresponded to the conjugate containing one $PEG_{10,000}$ unit per hGRF.

EXAMPLE 3b

Solution-Phase Pegylation of hGRF, using $PEG_{20,000}$

In this example a branched monomethoxy PEG having a molecular weight of 20,000 Dalton with lysine as spacer (supplied by Shearwater Polymers, Inc.) was used.

This branched PEG has been obtained by linking to each amino group of lysine a $PEG_{10,000}$.

The carboxy group of the spacer lysine, activated as succinimidyl ester, was reacted in DMSO to the amino groups of hGRF(1-29)-$NH_2$ using a molar ratio of 0.9 moles of PEG to 1 mole of GRF.

The solvent was removed by lyophylization and the residue fractionated by gel exclusion chromatography in a preparative column Superose 12 TM. A single peak was obtained, corresponding to the conjugate containing one $PEG_{20,000}$ unit per hGRF.

EXAMPLE 4

Analytical Characterization of the hGRF-PEG Conjugates

The products, obtained as previously reported, were examined for the bound PEG chains on the basis of the following assays:

1. Colorimetric method based on trinitrobenzene sulphonate was used for free amino groups determination (as described in Habeed et al., 1966);
2. Colorimetric method based on iodine assay was used for PEG content determination (as described in Sims et al., 1980);
3. PEG chain number based on norleucine as chain reporter in amino acid analysis was used (as described in Sartore et al., 1991);
4. Mass spectroscopy was used to determine the molecular weight of the conjugates.

The MALDI- mass spectrometry was used to reveal the molecular weight of the conjugates and their polydispersivity resulting from the polydispersivity of the starting PEG.

The PEG attachment site analysis of the hGRF-PEG conjugates was evaluated by amino acid sequence. Each sample was diluted 100-fold. Then 10 μl of this solution (about 50 pmol) loaded into the sequencer.

The purity of the final product was also confirmed by RP-HPLC analytical chromatography.

The analysis was carried out using a C18 analytical column (Vydac) eluted with a gradient $H_2O/0.05\%$ TFA (Eluent A) and acetonitrile/0.05% TFA (Eluent B) as follows:

| | |
|---|---|
| 0–5 min | 80% A |
| 5–50 min | 80% A → 5% A |
| 50–52 min | 5% A |
| 52–54 min | 5% A → 80% A. |

Flow rate 1 ml/min, loop 20 µl, UV-Vis. Detector at 226 nm.

The unconjugated hGRF eluted at 20.7 min.

Compound A1 eluted at 22.9 min, compound A2 eluted at 23.4 min, compound A3 at 24.4 min, and compound A4 at 25.5 min.

The conformational characterization of the "native" and polymer-bound peptides was performed by circular dichroism analysis.

Figure 4:
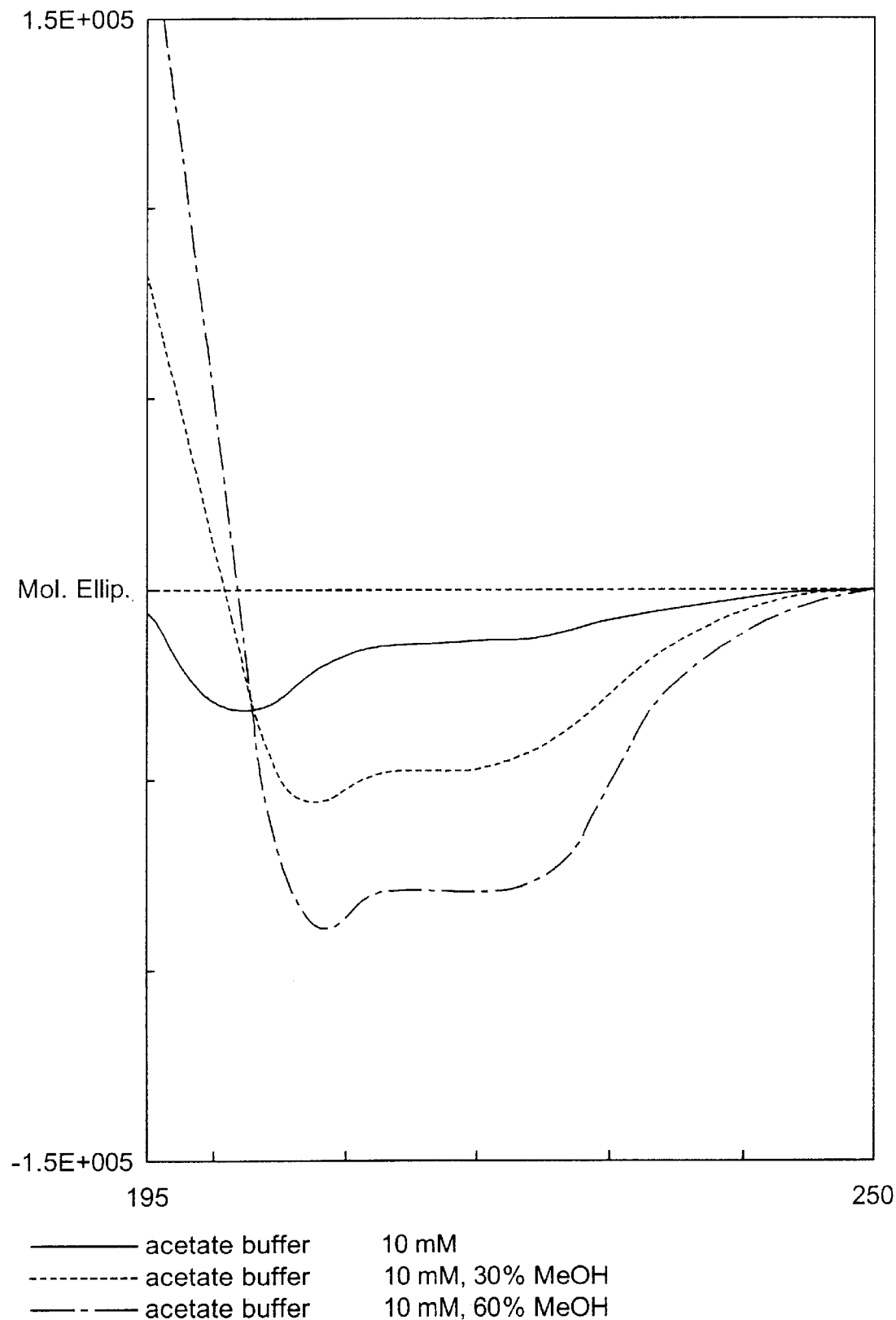
FIG. 4 shows the spectroscopic characterization of (Lys (MPEG$_{5,000}$-CH$_2$—CO—Nle—CO)$^{12,21}$-hGRF(1-29)NH$_2$) carried out by circular dichroism. The spectra are superimposable with those of "native" hGRF.

The spectroscopic characterization of the unconjugated hGRF and hGRF-PEG conjugates was carried out by circular dichroism analysis in the range of 190–300 nm. The samples (50 µg/ml) were dissolved in 10 mM acetic acid or methanol/10 mM acetic acid in 30:70 and 60:40 molar ratios. In all the above solutions the unconjugated hGRF and the hGRF-PEG conjugates presented a superimposable behavior, as shown in FIG. 4 for compound A3. In acetic acid solution the peptides were in random conformation, whereas by increasing the methanol content the peptide assumed an α-helix structure.

The results demonstrate that the PEG conjugation does not change markedly the structural properties of the peptide.

EXAMPLE 5
Stability Evaluation of the hGRF-PEG Conjugates

The proteolytic stability of hGRF and of the hGRF-PEG conjugates was investigated using proteolytic enzymes, such as subtilisin and chymotrypsin.

The study with subtilisin was performed by incubation at 4° C. of a 0.297 mM peptide solution in 0.1 M Tris HCl 0.05 M $CaCl_2$ pH 8.0 with a peptide/protease molar ratio 1:50,000.

In the case of chymotrypsin the peptide was dissolved in 0.08 M Tris HCl, 0.1 M $CaCl_2$ pH 7.8 and a peptide/protease molar ratio of 1:15,000 was used.

Figure 3A:
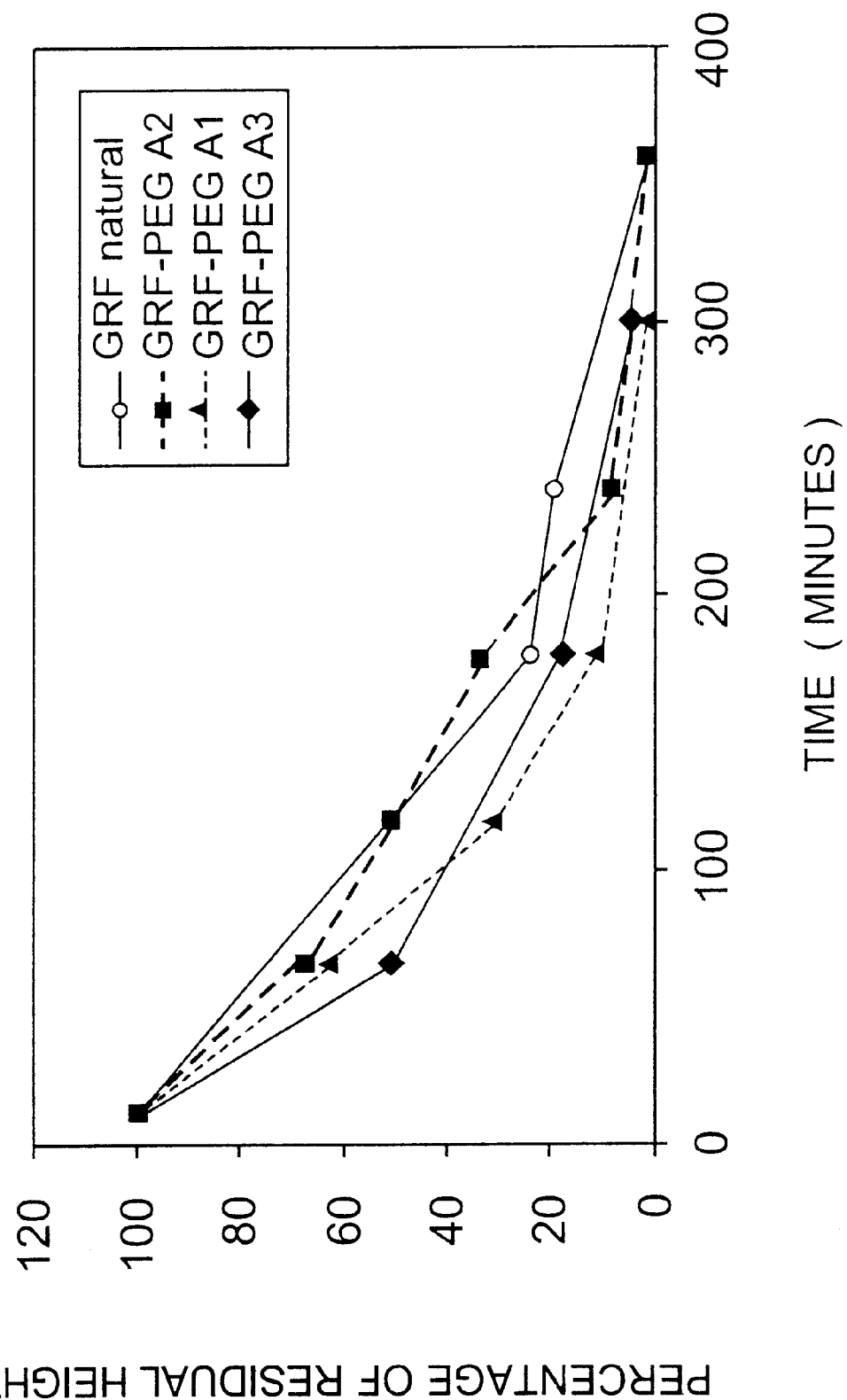
FIG. 3a reports the degradation of hGRF(1-29) and of the PEG conjugates of the present invention by subtilisin.
Figure 3B:
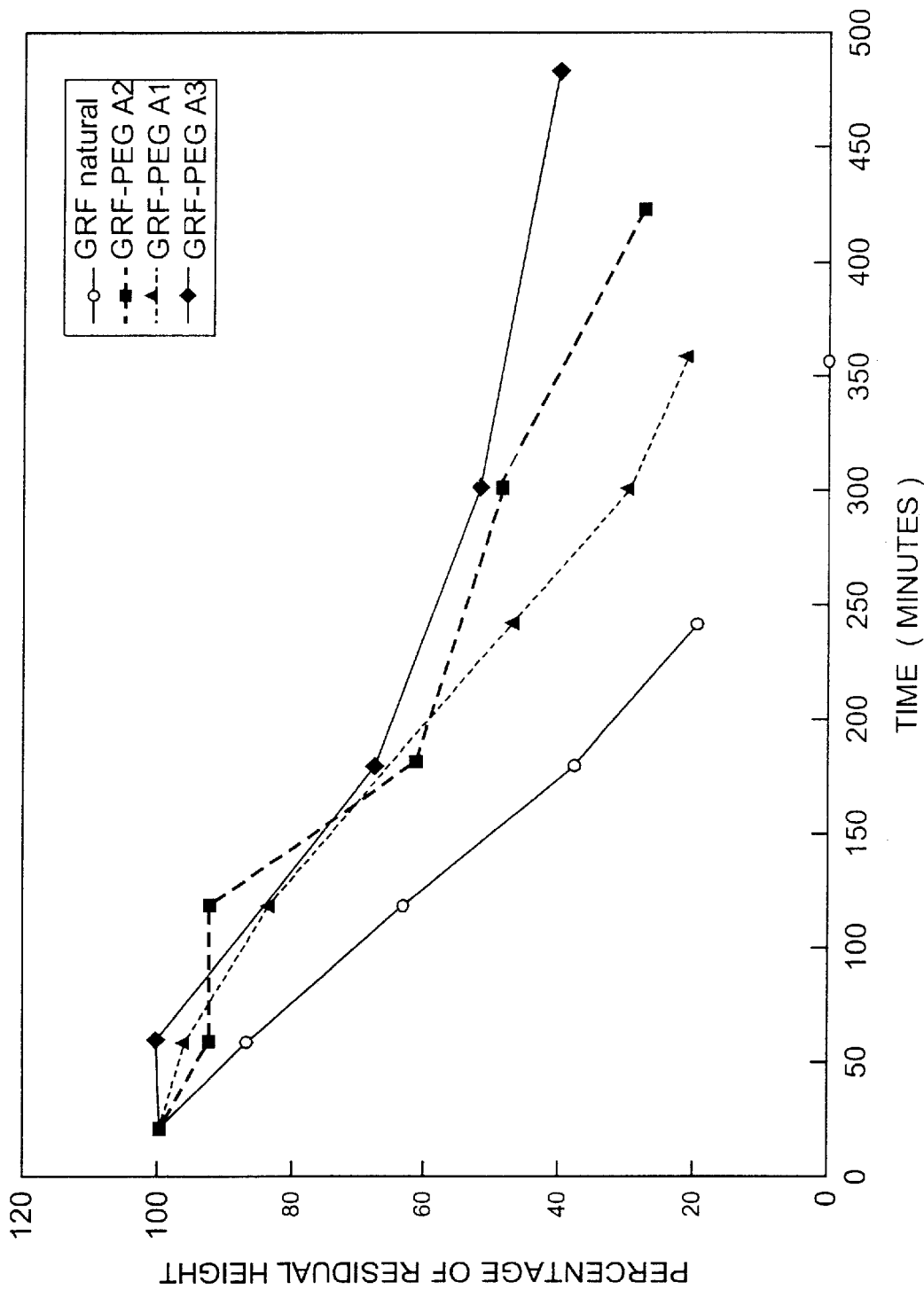
FIG. 3b reports the degradation of hGRF(1-29) and of the PEG conjugates of the present invention by chymotrypsin.

The degradation behavior was followed by analytical RP-HPLC using C18 column eluted under the same conditions as reported in Example 4. The height corresponding to the peak of the starting compound was calculated before incubation with the proteolytic enzyme and after scheduled times of incubation. The percentage of residual height at the scheduled times was estimated and is reported in FIGS. 3a and b.

EXAMPLE 6
Pegylation with Alkylating PEG hGRF was conjugated with mono-methoxylated PEG activated with different acylating groups as well as alkylating groups.

The alkylating PEG presents the advantage of yielding conjugates that maintain the positive charge at the lysine residue.

The isolation and characterisation were carried out as described in Examples 1–4.

EXAMPLE 7
Evaluation of the Activity of hGRF-PEG Conjugates

Materials

Test Compounds

Human $GRF_{1-29}$ hGRF(1-29)-$NH_2$, batch 1299201, supplied by Bachem;

Human $GRF_{3-29}$ hGRF(3-29), supplied by Bachem;

Human $GRF_{3-29}$, supplied by ISL; and hGRF-PEG Conjugates prepared as described above.

Reagents

CHO-hGRFR-LUC in vitro assay

MEM alpha medium with ribonucleosides and deoxyribonucleosides (Gibco) supplemented with 10% fetal bovine serum (Gibco) plus 600 µg/ml geneticin G418 sulfate (Gibco);

Cell culture lyses reagent (Promega);

Luciferase assay reagent (Promega); and

Luclite (Packard).

In Vitro Rat Pituitary Cell Bioassay

Earle's Balanced Salts (EBSS) (Gibco), supplemented with 50 µg/ml of gentamycine sulfate (Sigma).

Medium 199 (M199) with Earle's Salts (Gibco) with 12.5% of fetal bovine serum (FBS) (Gibco) and 50 µg/ml of gentamycine sulfate.

Rat GH assay kit supplied by Amersham.

Enzyme solution for tissue digestion (make up to 30 ml of EBSS):

120 mg Collagenase (Sigma)

30 mg Hyaluronidase (Sigma)

30 mg Dnase I (Sigma)

900 mg BSA (Sigma)

After reconstitution, the solution was filter-sterilized and placed at 37° C.

In Vivo Bioassay

Rat GH radioimmunoassay kit supplied by Amersham.

Human GRF(1-44) radioimmunoassay kit supplied by Phoenix Pharmaceutical.

Animals

SPF adult male Sprague-Dawley rats, 200–250 g b.w., supplied by Charles River, are used after an acclimatisation period of at least 7 days.

Methods

CHO-hGRFR-LUC in Vitro Assay

CHO-hGRFR-LUC (clone 1-11-20) is a cloned cell line that had been obtained by cotransfection of the pcDNA3-hGRF-R and pTF5-53 LUC vectors into CHO-DUKX cell line.

Figure 12:
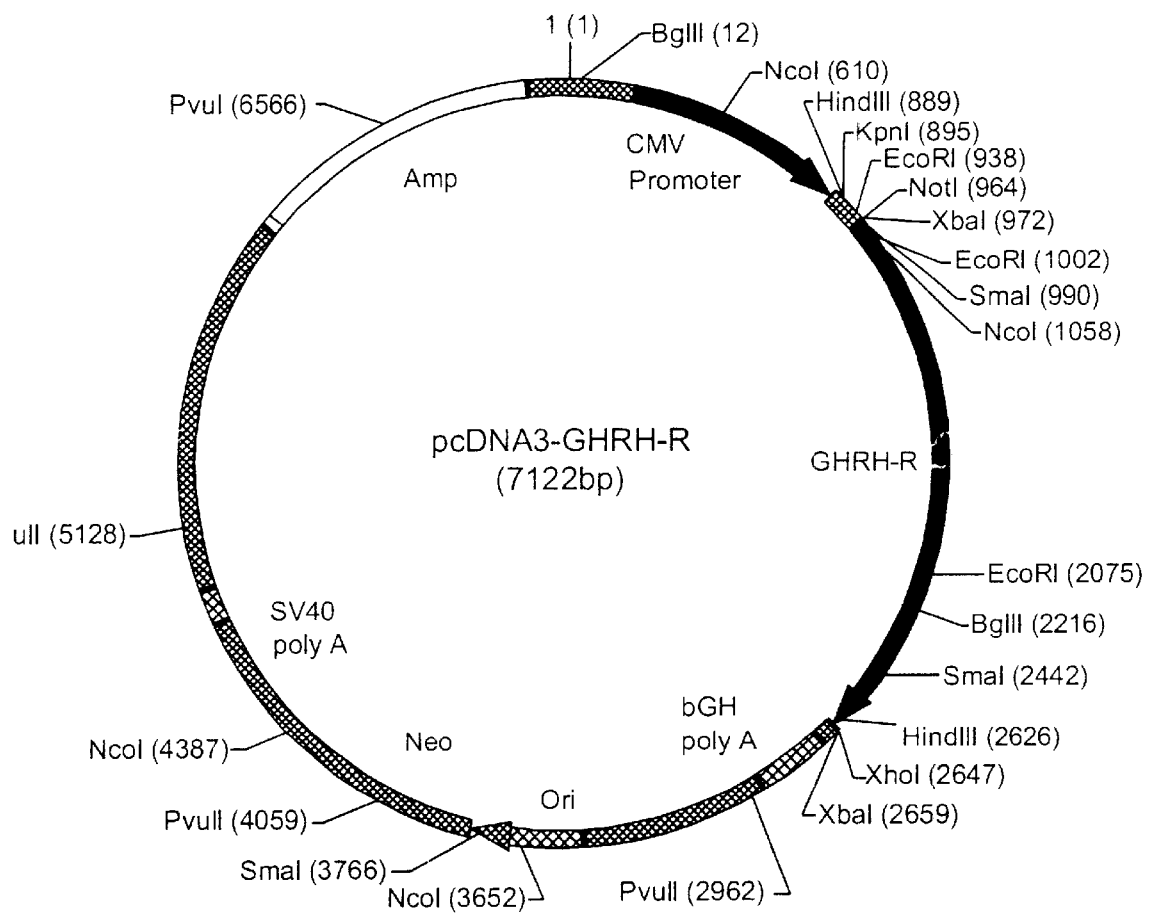
FIG. 12 represents the restriction map of plasmid pcDNA3-hGRF-R used in the reporter gene assay for the evaluation of GRF activity.

The plasmid pcDNA3-hGRF-R was constructed by inserting the human growth hormone releasing factor receptor (hGRF-R) cDNA into pcDNA3 expression vector. The Bluescript plasmid containing hGRF-R cDNA was kindly provided by Dr. B. Gaylinn (University of Virginia) the pcDNA3 mammalian expression vector was obtained from Invitrogen. The hGRF-R coding sequence was driven by the human cytomegalovirus (CMV) promoter. Its restriction map is reported in FIG. 12.

Figure 13:
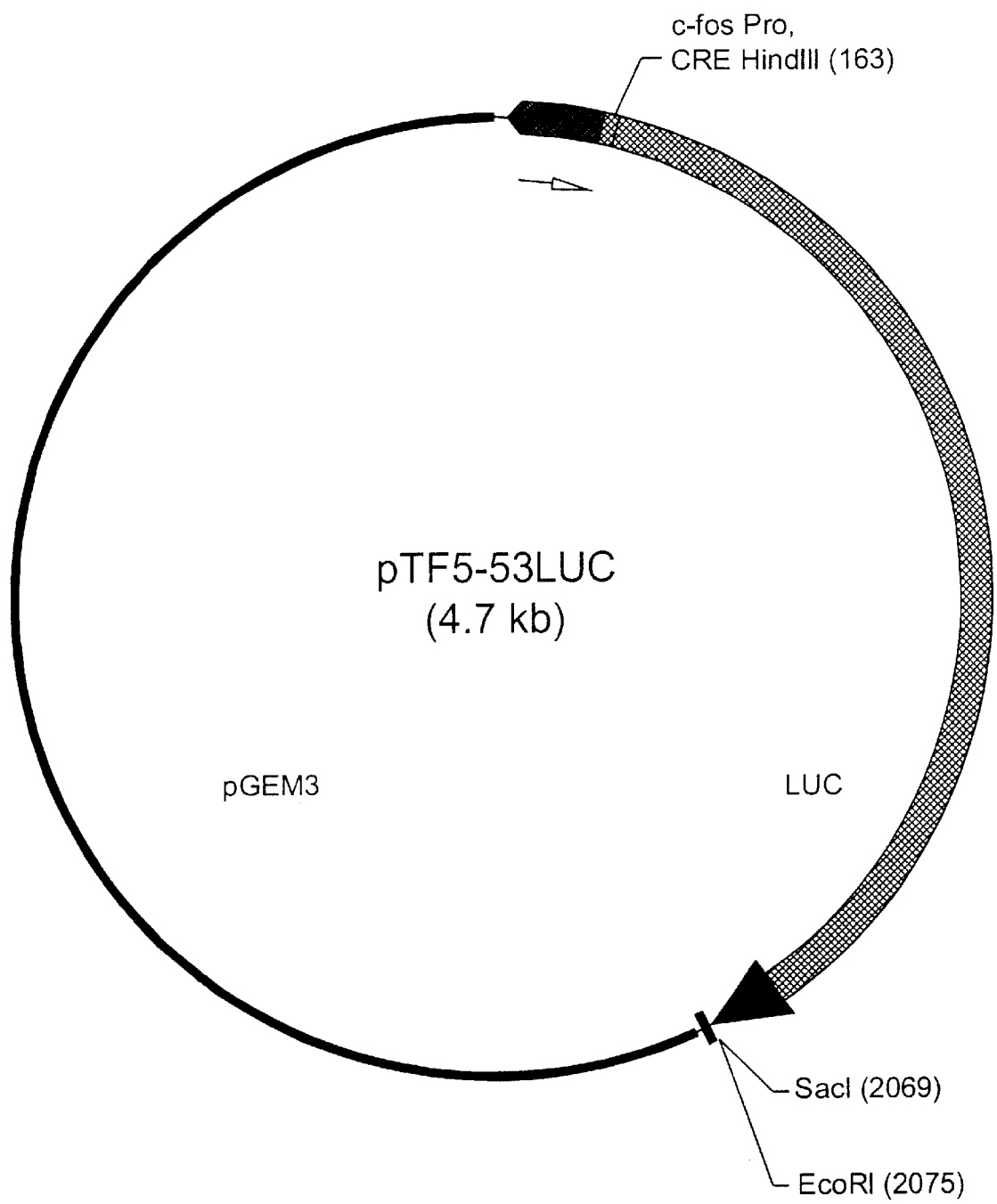
FIG. 13 shows the restriction map of plasmid pTF5-53 LUC used in the reporter gene assay for the evaluation of GRF activity.

The plasmid pTF5-53LUC was constructed by inserting the c-fos cAMP response element along with its endogenous promoter upstream of the luciferase coding sequence in plasmid poLuc. The cAMP response element and the c-fos promoter were obtained from the plasmid pTF5-53 (described in Fish et al, 1989). The promoterless reporter gene vector (poLuc) with multiple cloning sites upstream of the luciferase coding sequence was obtained from Dr. Brasier (University of Texas, Galveston). Its restriction map is reported in FIG. 13.

These CHO-DUKX cells obtained by the above co-transfection were routinely grown in MEM alpha medium containing ribonucleosides and deoxyribonucleosides and supplemented with 10% fetal calf serum plus 600 µg/ml geneticin G418 sulfate.

The cells were seeded (40,000 cells/well) in white 96-well plates (Dynatech) and incubated for 16–18 hrs in 200 µl growth medium before the assay.

The next day, the medium was removed and replaced with a medium containing different concentrations of hGRF(1-29) in-house reference standard (Bachem) or different hGRF-PEG conjugates before incubating the plates at 37° C., 5% $CO_2$ for two hours. At the end of incubation, CHO-hGRFR-LUC cells were washed twice with 200 µl of PBS (Sigma) and then lysed by adding 50 µl of a cell culture lyses reagent (Promega) to each well. After a further 15-minute incubation at room temperature. the plates were read in a luminometer (Dynatech) after introducing 150 µl of a luciferase assay reagent (Promega)

As an alternative method, CHO-hGRFR-LUC cells, seeded at 50,000 cells/well, at the end of incubation with different hGRF-PEG conjugates, were washed with PBS, as above discussed. To each well 100 µl PBS containing calcium and magnesium ions was added, prior to addition of 100 µl of Luclite (Packard). After 10 minutes incubation at room temperature, plates were read in luminometer (Lumicount—Packard).

Results were expressed as relative light unit (RLU).

In vitro Rat Pituitary Cell Bioassay for hGRF(1-29)

The animals (SPF male Sprague-Dawley rats 200 g, b.w.) were sacrificed by $CO_2$ inhalation and the pituitaries removed. The tissue was finely minced and put into a bottle with the enzyme solution for tissue digestion. The bottle was placed in an incubator at 37° C. for 1 hour.

The digested tissue was recovered and the cells washed twice, counted and adjusted to a concentration of $5 \times 10^5$/ml. The cells were plated out in a 48-well plate (200 µl/well) and the plate placed in an incubator for 72 hrs.

After 72 hrs the cells were incubated with different concentrations of hGRF for 4 hours. At the end of the incubation period the supernatants were collected and stored at −80° C.

The GH content in each sample was assayed by a commercial rat GH radioimmunoassay kit.

In vivo Assay

The animal was injected i.v. with hGRF(1-29)(400 µg/rat). A few minutes before blood collection, the animal was anaesthetized (ketamine-xylazine). Two ml of blood were withdrawn from the inferior vena cava from each rat. The sample was divided into two aliquots: 1 ml was collected as such and serum was obtained after an incubation period of about 3 hours at 37° C. and subsequent centrifugation; the remaining 1 ml was collected into a vial containing 50 µl of a 4 mg/ml heparin solution, immediately stored on ice and plasma was obtained after centrifugation at 4° C.

Blood samples were collected at different time points from the injection of the test compound using different animals. in each experimental session a total of three rats for each time point was used.

Plasma and serum samples were immediately frozen and stored at −20° C.

GH serum levels were measured by a commercial RIA kit; hGRF plasma levels were measured by a commercial RIA kit for hGRF(1-44).

Results

NOTE: throughout this section and the related Figures "GRF-1PEG $1^{st}$ peak" corresponds to $(Lys(MPEG_{5,000}\text{-}CH_2\text{—CO—Nle—CO})^{21}\text{-hGRF(-1-29)-NH}_2)$, "GRF-1PEG $2^{nd}$ peak" corresponds to $(Lys(MPEG_{5,000}\text{-}CH_2\text{—CO—Nle—CO})^{12}\text{-hGRF(1-29)-NH}_2)$, "GRF-2PEG" corresponds to $(Lys(MPEG5,000\text{-}CH_2\text{—CO—Nle—CO})^{12,21}\text{-hGRF(1-29NH}_2)$ and "GRF3PEG" corresponds to $N^{\alpha}\text{-}(MPEG_{5,000}\text{-}CH_2\text{—CO—Nle—CO})(Lys(MPEG_{5,000}\text{-}CH_2\text{—CO—Nle—CO})_{12,21}\text{-hGRF(1-29)-NH}_2)$.

CHO-hGRFR-LUC in Vitro Assay

Figure 5:
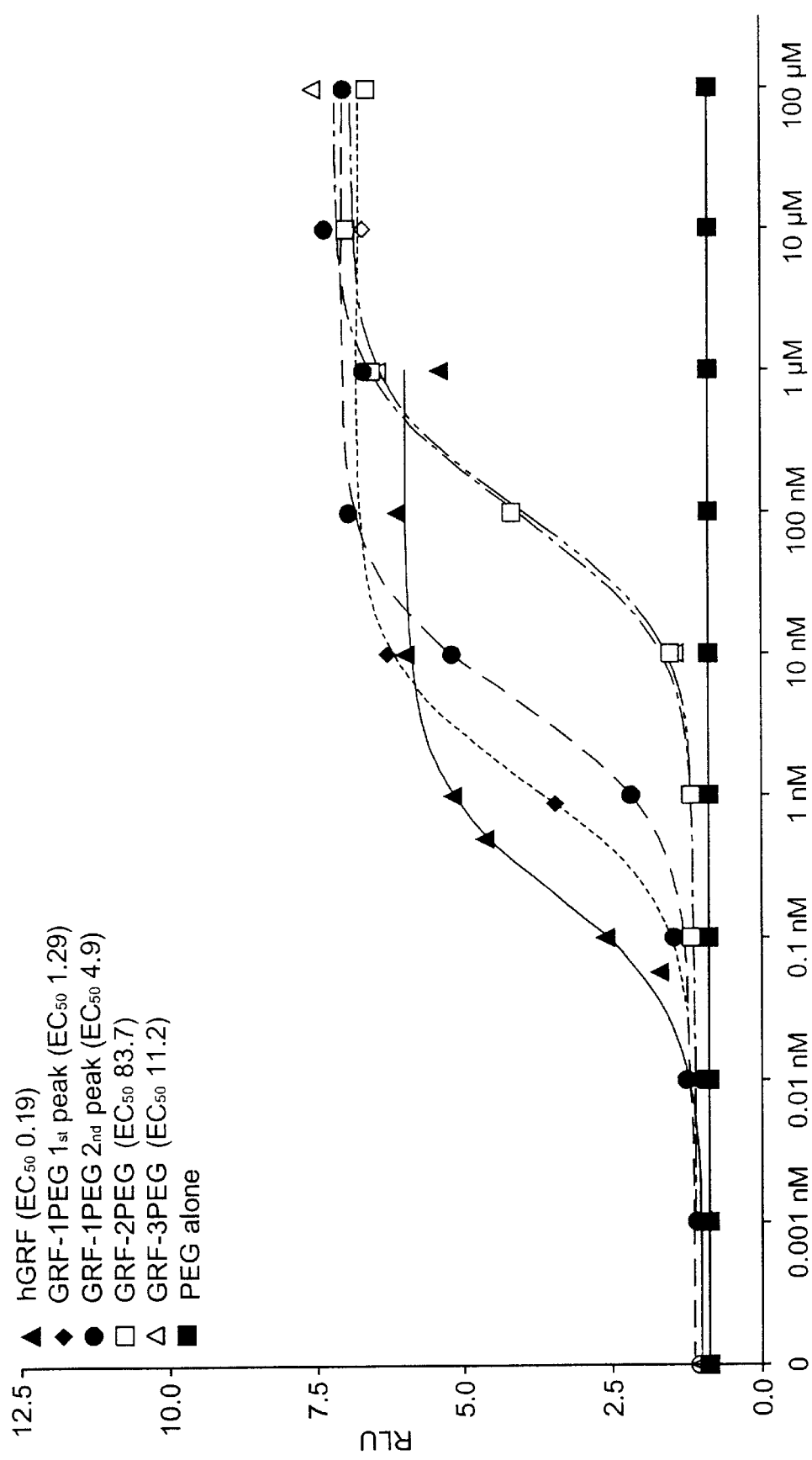
FIG. 5 shows the biological effect of various hGRF-PEG conjugates (from a 1st DMSO preparation) in the CHO-hGRFR-LUC in vitro assay. Data represent the average of three independent experiments.
Figure 6:
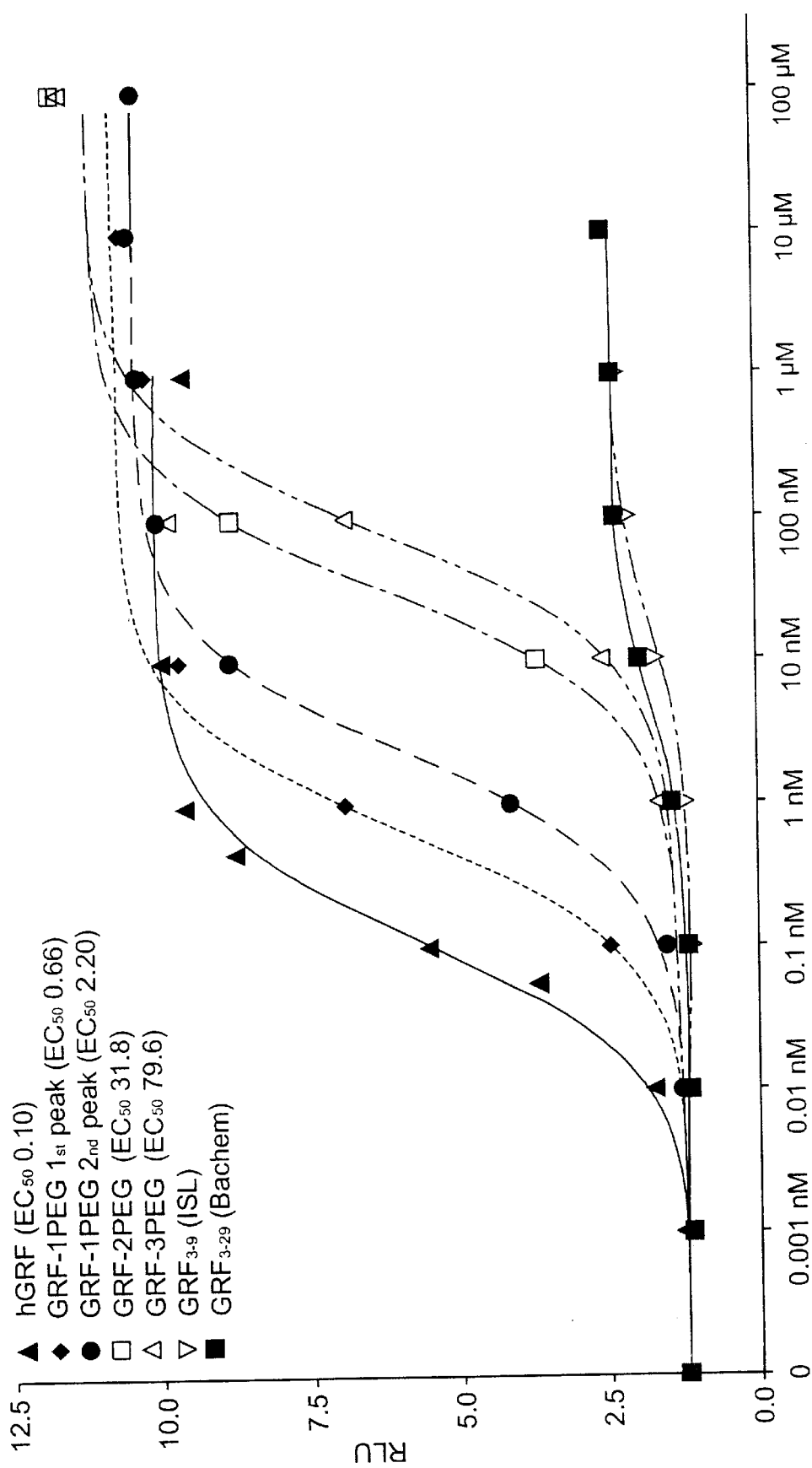
FIG. 6 reports the biological effect of various hGRF-PEG conjugates (from a 2nd DMSO preparation) in the CHO-hGRFR-LUC in vitro assay. Data represent the average of two independent experiments.

The activities of two different batches of hGRF-PEG conjugates, both prepared using DMSO, in the CHO-hGRFR-LUC in vitro assay were shown in FIGS. 5 and 6.

All preparations were found to be active although to a lesser extent as compared to "native" hGRF (hGRF subjected to the same purification steps used for the pegylated compounds), with GRF-1PEG (both the $1^{st}$ and $2^{nd}$ peak) being more active than the GRF-2PEG and GRF-3PEG. No difference was observed between hGRF and "native" hGRF (data not shown).

Figure 7:
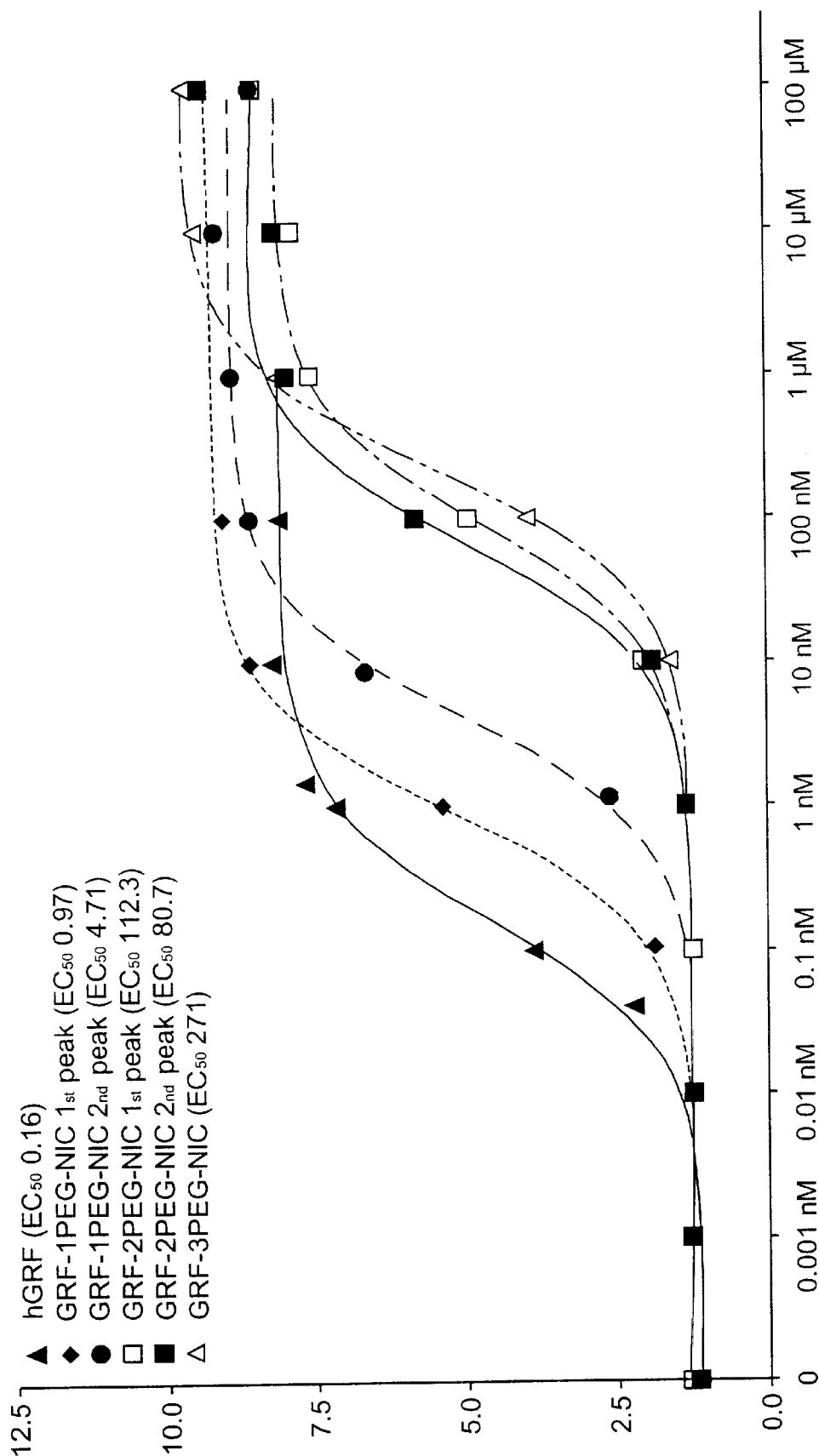
FIG. 7. shows the biological effect of various hGRF-PEG conjugates (from a nicotinamide preparation) in the CHO-hGRFR-LUC in vitro assay. Data represent the average of two independent experiments.

A similar in vitro bioactivity of the hGRF-PEG conjugates from both DMSO-prepared batches (FIG. 5 vs FIG. 6) as well as the conjugates from the batch prepared using nicotinamide solution (FIG. 7) were observed. FIG. 6 also shows that two different hGRF(3-29) preparations did not possess a significant it/ vitro activity as compared to hGRF(1-29).

In vitro Rat Pituitary Cell Bioassay for $hGRF_{1-29}$

Figure 8:
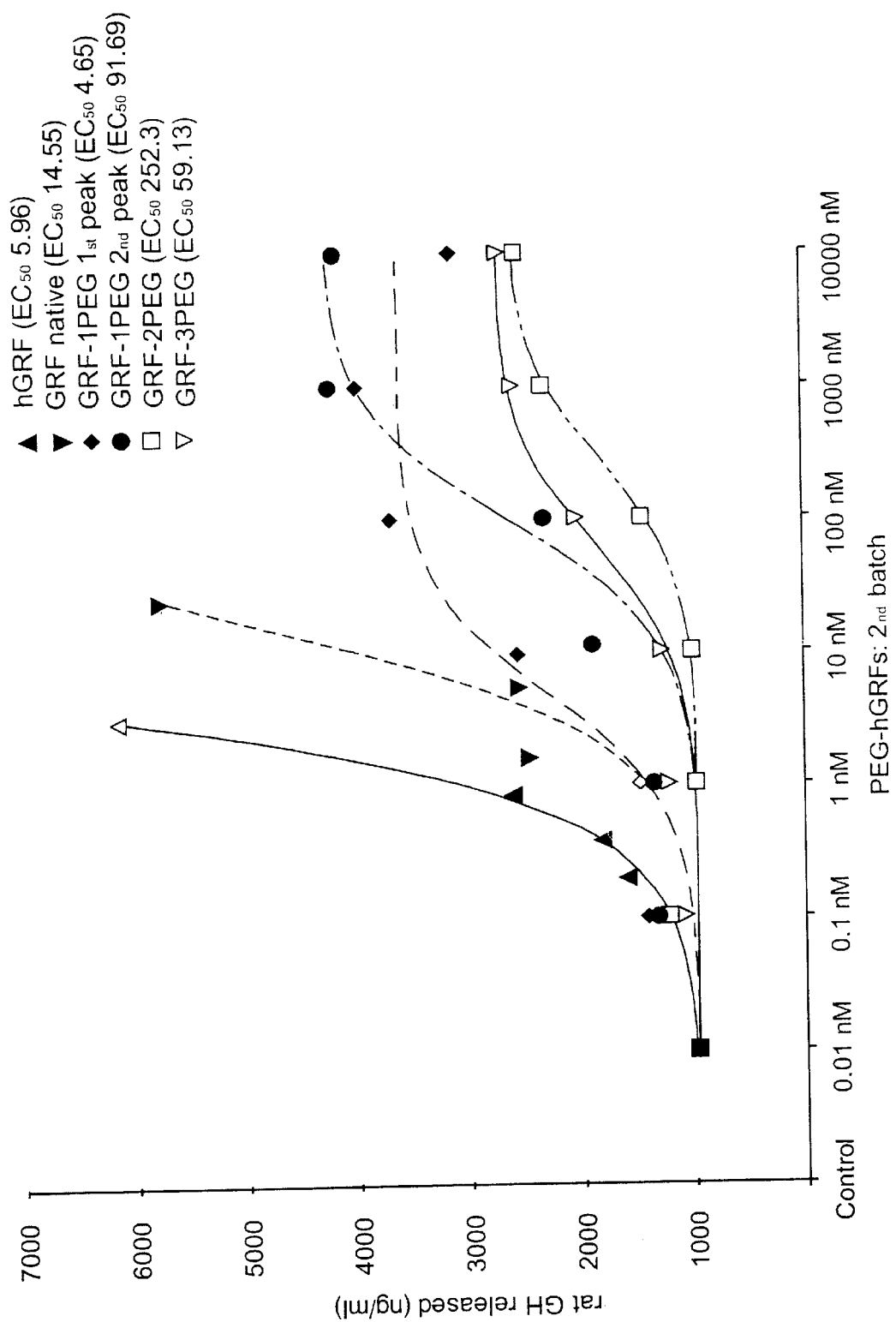
FIG. 8 illustrates the biological effect of various hGRF-PEG conjugates (1st DMSO preparation) on the GH release from rat pituitary cell in vitro.
Figure 9:
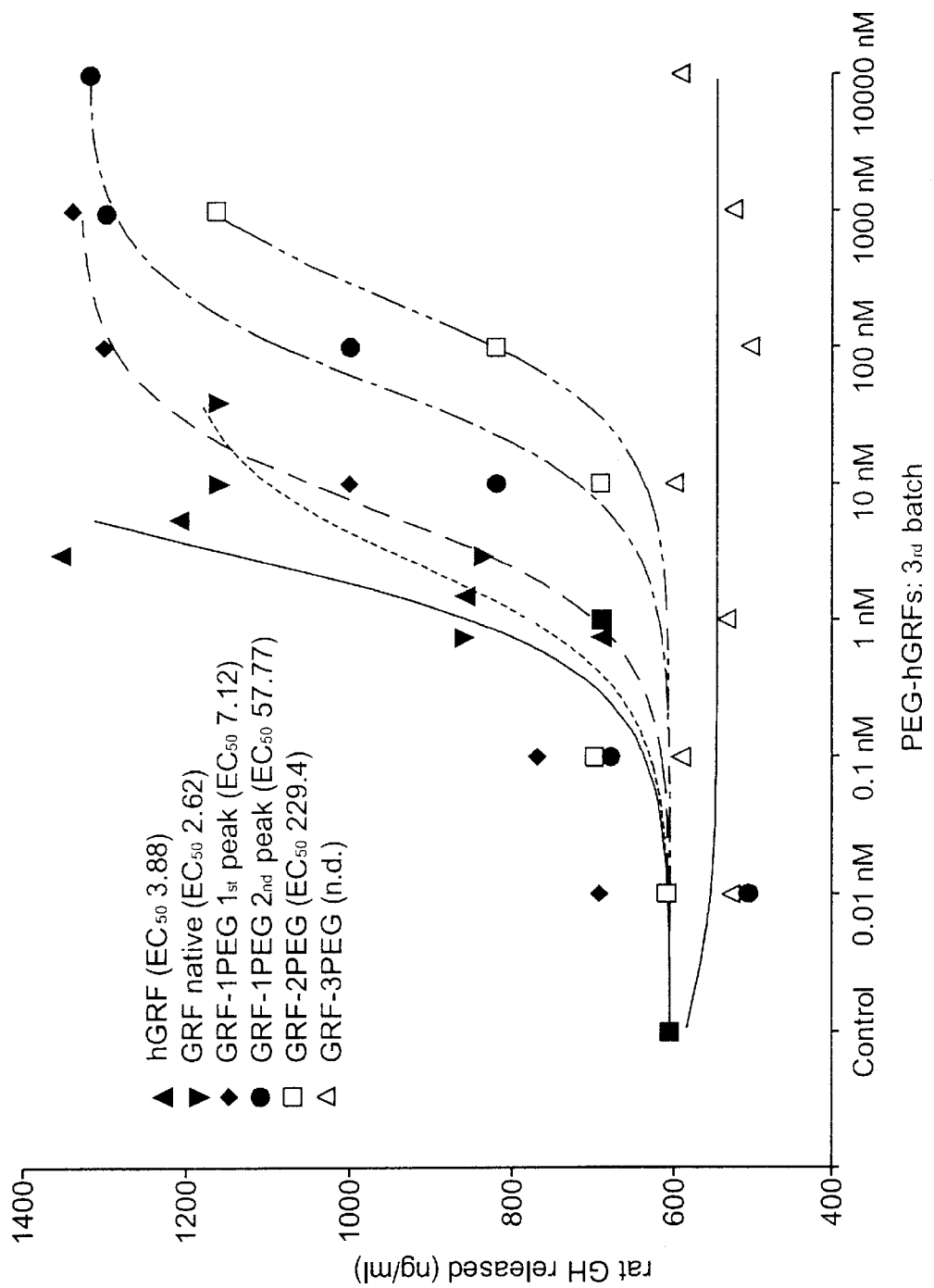
FIG. 9 shows the biological effect of various hGRF-PEG conjugates (from a 2nd DMSO preparation) on the GH release from rat pituitary cell in vitro.

In both assays performed with hGRF-PEG conjugates from two DMSO preparations, the GRF-1PEG 1st peak was found to be the most active compound. followed by GRF-1PEG 2nd peak, GRF-2PEG and then GRF-3PEG (FIGS. 8 and 9). These findings are in good agreement with those obtained in the reporter gene assay.

In vivo Assay

Figure 10:
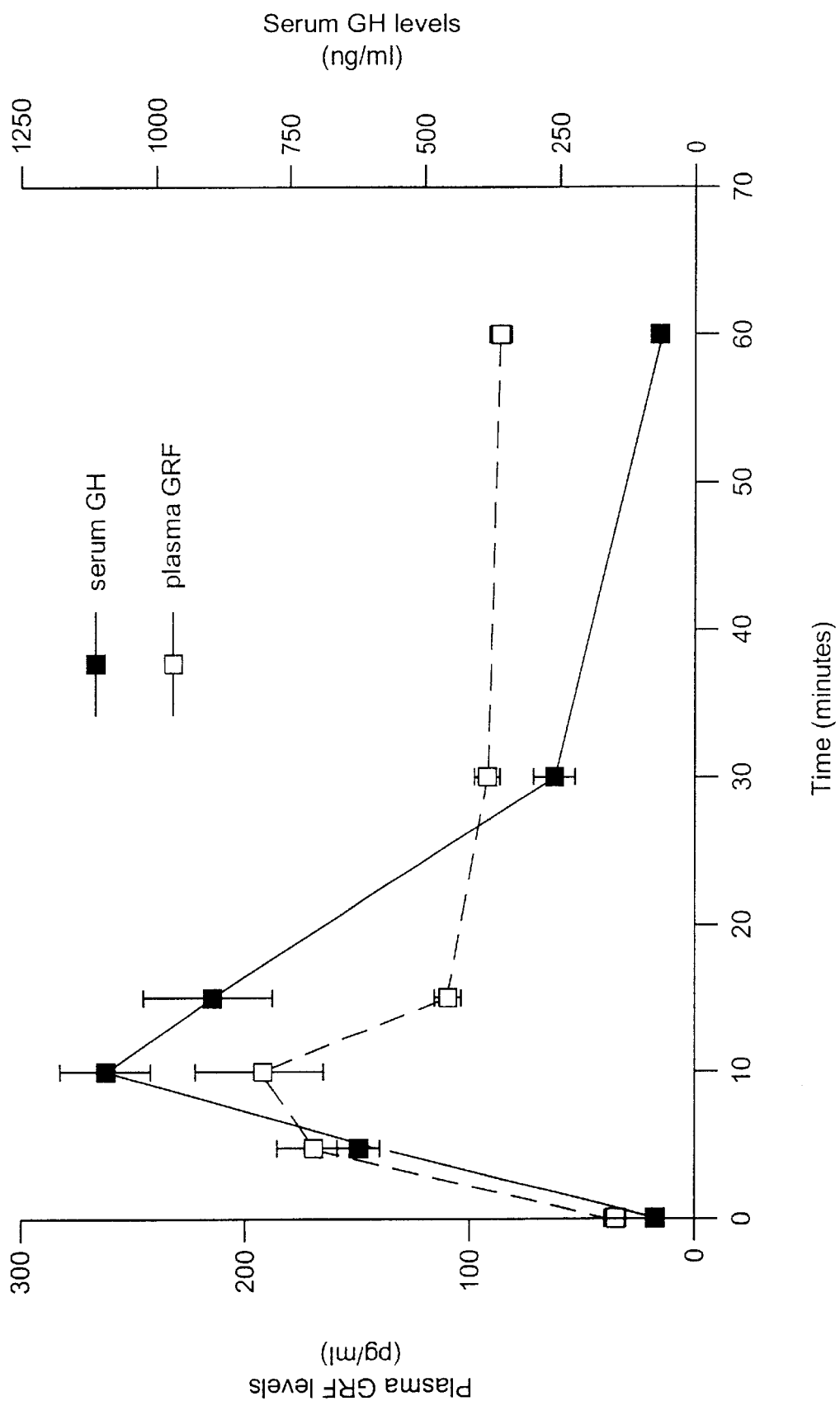
FIG. 10 shows the time-response curve of plasma hGRF and serum GH levels following hGRF (400 $\mu$g/rat) i.v. injection in male rats. Each point represents the mean ±SEM value obtained from nine rats.

In preliminary experiments the serum GH and plasma hGRF levels were determined in rats following i.v. injection of 400 µg of hGRF. The relevant results are illustrated in FIG. 10. As shown, both GH and hGRF peaked at 10 min after hGRF injection. Thereafter, serum GH concentrations rapidly declined and returned to basal levels after 60 min, whereas the plasma hGRF concentrations maintained a sustained level in the same time-interval.

Figure 11:
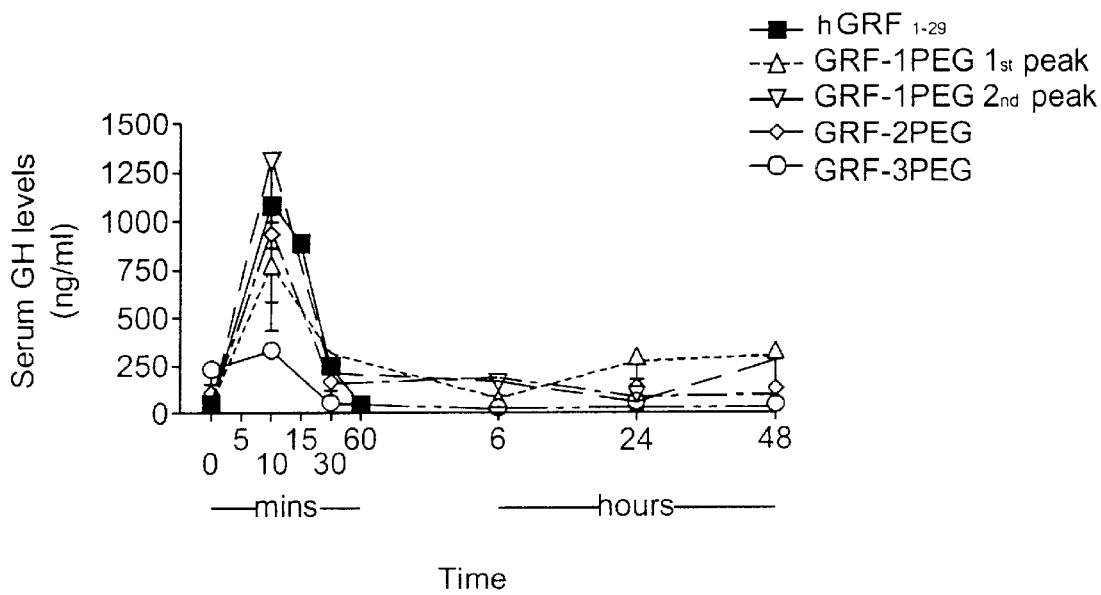
FIG. 11A (see the first graph on the page) shows the time-response curve of serum GH levels after the i.v. injection of 400 $\mu$g/rat of hGRF-PEG conjugates (DMSO preparation) in male rats. Each point represents the mean value obtained for three rats.
FIG. 11B (see the second graph on the pace) shows the time-response curve of plasma hGRF levels after the i.v. injection of 400 µg/rat of hGRF-PEG conjugates (DMSO preparation) in male rats. Each point represents the mean value obtained for three rats.
Figure 11:
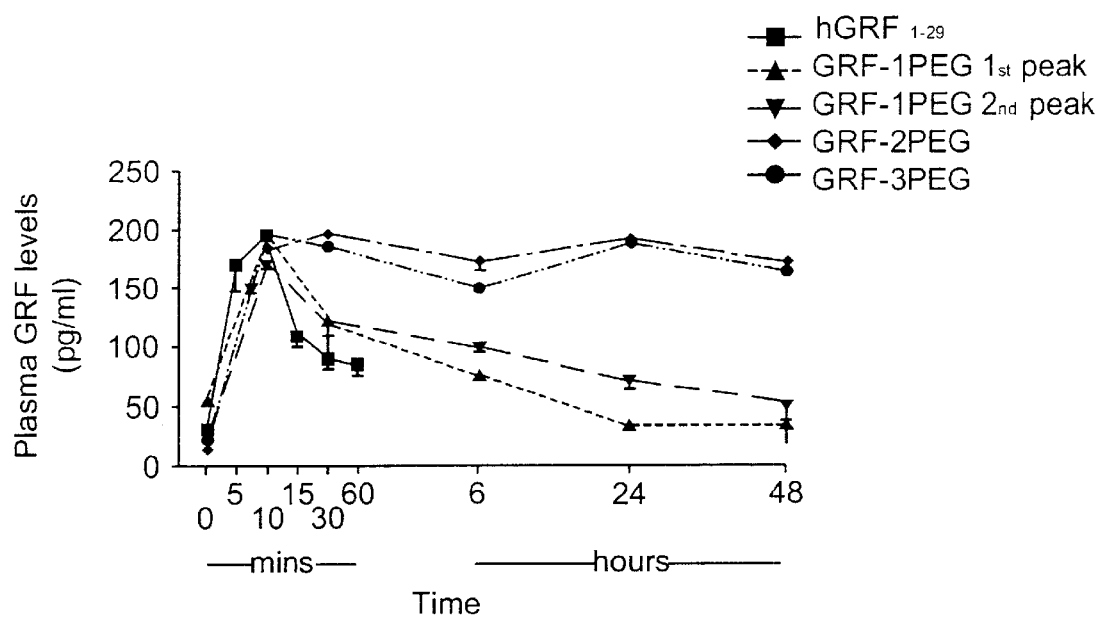

In FIGS. 11A and 11B the blood levels of GH and GRF at different time-points up to 48 hours in rats treated with 400 µg i.v. of GRF-1PEG $1^{st}$ and $2^{nd}$ peak, GRF-2PEG and GRF-3PEG (DMSO preparations) are reported.

All the pegylated preparations induce a GH serum peak 10 minutes after their i.v. injection similarly to the $hGRF_{1\text{-}29}$. However, while the GRF-1PEG $1^{st}$ and $_2^{nd}$ peak and GRF-2PEG induce GH levels comparable to those obtained with $hGRF_{1\text{-}29}$, GRF-3PEG confirms its lower activity as found in vitro.

For what the GRF plasma levels are concerned, a completely different pattern is observed with GRF-1PEG $1^{st}$ and $2^{nd}$ peaks as compared to GRF-2PEG and GRF-3PEG irrespective of the preparation (DMSO or nicotinamide) used. At 48 hours following the injection of GRF-1PEG $1^{st}$ and $2^{nd}$ peaks, the GRF plasma concentrations return to basal value, whereas more sustained levels are obtained with GRF-2PEG and GRF-3PEG.

EXAMPLE 8

Solid-Phase Synthesis of Site-Protected hGRF(1-29)-$NH_2$ Derivatives as Starting Compounds in the Pegylation Process A solid-phase synthesis of hGRF(1-29)-$NH_2$ derivatives containing a specific protection group (the N-allyloxycarbonyl-group) at the primary amino groups of both Lysine 12 and 21 has been carried out. This is to allow site-specific pegylation at the $N^{\alpha}$-terminus. Another amino-protected derivative is prepared by blocking the $N^\alpha$-terminus through acylation and the Lysine 12 with the N-allyloxycarbonyl group. This derivative is used for site-specific pegylation at Lysine 21.

Material and Methods

Peptide Synthesis Procedures

All hGRF derivatives peptide-resins were initially assembled using Fmoc chemistry on an Applied Biosystems Inc. Model 431A Peptide Synthesizer, using a low substitution (0.16 mmol/g) PAL-PEG-PS resin and a double-couple and capping protocol for each residue to optimize the amount and purity of the crude product. Additionally (N-isopropyl-Tyr$^1$, Lys(Alloc)$^{12}$)-hGRF(1-29)-NH$_2$ peptide-resin was manually treated with a reductive alkylation procedure to add an N-terminal isopropyl group.

All peptide resins were cleaved with a mixture of TFA/1.2-ethanedithiol/thioanisole/water (10:0.5:0.5:0.5 (v/v)) for 2 hours, and the crude peptides isolated by precipitation in MTBE and centrifugation. Lyophilized crude peptides were purified by reversed-phase gradient HPLC using a Vydac C18 Preparative column with a 0.1% TFA Water/Acetonitrile buffer system. All purified peptides were characterized by Analytical Reversed-Phase HPLC and MALDI-TOF Mass Spectrometry.

Materials

Fmoc-L-Amino Acids (Bachem Bioscience, Perseptive Biosystems, NovaBiochem). DMF, 20 liter drum (J. T. Baker), Piperidine (Applied Biosystems, Chem-Impex), HBTU (Rainin, Richelieu Biotechnologies), NMM (Aldrich), Acetic Anhydride (Applied Biosystems), Resins (Perseptive Biosystems, NovaBiochem). a-Cyano-4-hydroxy-cinnamic acid (Sigma), Sinapinic acid (Aldrich), acetonitrile (J. T. Baker), TFA (Sigma, Pierce), deionized H$_2$O Millipore Milli-Q Water System). The other solvents and reagents are listed as follow:

| REAGENTS/SOLVENTS | VENDORS |
| --- | --- |
| NMP | Applied Biosystems Inc., J.T Baker |
| HBTU | Applied Biosystems Inc., Richelieu Biotechnologies Inc. |
| 0.5 M HOBt in DMF | Applied Biosystems Inc. |
| 2.0 M DIEA in NMP | Applied Biosystems Inc. |
| Piperidine | Applied Biosystems Inc. |
| Dichloromethane | Applied Biosystems Inc. |
| Acetic Anhydride | Applied Biosystems Inc. |

Amino acids: most FMOC amino acids used on the ABI 431A synthesizer were purchased from Applied Biosystems as pre-weighed 1.0 mmol cartridges. FMOC-Lys(Alloc)-OH was purchased from Perseptive Biosystems (Framingham, Mass.) in bulk and the cartridges filled in house. All amino acids used were of the L-configuration.

Resins: the primary resins used for the hGRF analogs were PAL-PEG-PS (Peptide Amide Linker—Polyethylene Glycol—Polystyrene) resins. The PAL-PEG-PS supports, purchased from PerSeptive Biosystems, consistently show superior results in purity and yield of crude product. A low substitution resin of 0.16 mmol/g was used for all derivatives. Lower substitution resins are commonly used for long, difficult sequences to ensure better coupling by decreasing steric hindrance and β-sheet formation in the growing peptide chains.

Methods

Chain Assembly—Applied Biosystems Inc. Model 431A Peptide Synthesizer

Protected peptide chains are initially assembled using FMOC strategy on an Applied Biosystem Inc. Model 431A Peptide Synthesizer, which utilizes programmed fast FMOC cycles (FastMoc™). HBTU is used for activation and coupling, 20% Piperidine for deprotection, and NMP is the main solvent used during deprotection, amino acid dissolution and washing of the resin. Amino acids are introduced in pre-weighed 1.0 mmol cartridges. The 0.25 mmol Fast-Moc™ cycles use 1.0 mmol cartridges and a 40 ml reaction vessel.

Chain Assembly—Procedure

The steps for the 0.25 mmole scale programmed cycles can be summarized as follows:

1. Piperidine Deprotection—The resin is first washed with NMP, then an 18% piperidine/NMP if solution is delivered and deprotects for 3 minutes. The reaction vessel is drained and a 20% piperidine solution is delivered and deprotection continued for approx. 8 minutes.
2. Dissolution of Amino Acid—NMP (2.1 g.) and 0.9 mmol of 0.45 M HBTU/HOBt in DMF (2.0 g.) are added to the cartridge and mixed for 6 minutes.
3. NMP washes—The reaction vessel is drained and the resin is washed 5 times with NMP.
4. Activation of amino acid and transfer to reaction vessel (RV)—1 ml of 2 M DIEA in NMP is added to the cartridge to begin activation of the dissolved amino acid, then transferred from the cartridge to the RV.
5. Coupling and final washing—The coupling reaction between the activated amino acid and the N-terminal deprotected peptide-resin proceeds for approx. 20 minutes and then the RV is drained and the resin washed with NMP.
6. Capping (if desired)—Approx. 12 ml of a 0.5 M Acetic Anhydride, 0.125 M DIEA and 0.015 M HOBt in NMP solution is added to the reaction vessel and vortexed for 5 mins. This should acetylate any uncoupled sites on the resin, resulting in truncated rather than deletion sequences, which simplifies later purification steps.

The complete protocol for these cycles can be found in Applied Biosystems User Bulletin No. 35 (FastMoc™ 0.25 and 0.10 on the Model 431A).

The Standard Protocol Steps for a Typical Synthesis:

Step 1. Wash resin 3X with DMF
Step 2. Deprotect 2X for 5 minutes with 20% Piperidine/DMF
Step 3. Wash resin 6X with DMF
Step 4. Couple for 45 minutes with Amino Acid activated with HBTU/NMM in DMF.
Step 5. Wash resin 3X with DMF For difficult sequences, an extra capping, step can be inserted after coupling, which uses 70% Acetic Anhydride in DMF for 20 minutes to acetylate any uncoupled sites on the peptide-resin, resulting in truncated sequences rather than deletion sequences in the final crude product.

Cleavage/Extraction

The cleavage cocktail used for removing side-chain protecting groups and releasing the peptide from the resin is a standard mixture used for peptides containing Arginine and/or Methionine. For 0.1–1.5 g peptide-resin, 10 ml Trifluoroacetic Acid, 0.5 ml D.I. Water, 0.5 ml Thioanisole, 0.5 ml Ethanedithiol (87% Trifluoroacetic Acid, 4.3% D.I. Water, 4.3% Thioanisole, 4.3% Ethanedithiol)

Cleavage Procedure 100 mg–1 g of peptide-resin is placed into a 20 ml glass vessel and cooled in an ice bath. The cleavage cocktail is prepared and also cooled in an ice bath, then added to the peptide-resin for a final volume of approx. 10 ml.

The vessel is removed from the ice bath and allowed to warm to room temperature. The vessel is capped and the reaction mixture stirred at room temperature for 2 hours.

After 2 hours, the solution is vacuum filtered through a medium-to-course porosity filter into approx. 30 ml of cold MTBE. The reaction vessel is washed with 1 ml TFA and filtered through the same filter funnel into the cold MTBE. The entire suspension is then transferred to a 50 ml centrifuge tube and centrifuged for approx. 10 minutes at 2,000 rpm at room temperature. The supernatant is aspirated, the precipitate re-suspended in 40 ml cold MTBE and centrifuged again. This step is repeated once more. The final supernatant is aspirated and the precipitate is purged with nitrogen to evaporate most of the remaining ether.

The peptide is then dissolved in 20–30 ml of aqueous 1%–10% Acetic Acid, diluted to approx. 100–150 ml with deionized water, shell frozen, and lyophilized.

Purification

RP-HPLC Methods
System—Waters Delta Prep 4000
Column—Vydac reversed-phase C18, 10 $\mu$m, 2.2×25 cm (Cat No. 218TP1022)
Buffers—A: Water/0. 1% TFA B: Acetonitrile/0.1% TFA
Flow Rate—15 ml/minute
Detection—Waters 484 UV detector, 220 nm
Gradient—Variable usually 0.2% B/min up to 1.0% B/min.

Lyophilized crude peptides are prepared by dissolving 50–100 mg of peptide in 200 ml of aqueous 0.1% TFA. The peptide solution is then loaded directly onto the preparative column through the "A" buffer reservoir line and the gradient program started.

Collected fractions are run overnight on an autosampler analytical HPLC system. Overlapping fractions judged to be >92% pure by peak integration are pooled, diluted 4:1 with D.I. Water, shell frozen, and then lyophilized on a Virtis 25 SL Freezedryer.

Characterization

Reversed-Phase HPLC
 Conditions:
System—Waters 510 pumps, 717 Autosampler, 490 Multiwavelength UV Detector
Column—Vydac C18, 5 $\mu$m, 0.46×25 cm (Cat. No. 218TP54)
Buffers—A: $H_2O$/0.1% TFA B: ACN/0.1% TFA
Flow Rate—1 ml/minute
Detection—UV: 214 nm, 280 nm
Gradient—2% B/minute Purified lyophilized peptide samples are prepared by dissolving 0.2–1.0 mg of peptide in aqueous 0.1% TFA to a concentration of 0.5–1.0 mg/ml.

15–18 $\mu$l are injected onto the column and eluted with a gradient program of 0–50% ACN in 25 minutes. Chromatogram data is collected and stored with the Waters Expert-Ease software system.

Mass Spectrometry
Type: MALDI-TOF (Matrix-assisted laser desorption/ionization Time-of-flight)
System: Perseptive Biosystems Voyager Elite
Matrices: α-Cyano 4-hydroxy cinnamic acid, 10 mg/ml in 67% ACN/0.1% TFA or Sinapinic Acid, 10 mg/ml in 50% ACN/0.1% TFA.

Peptide samples are prepared at 1–20 $\mu$mol conc. in 50% ACN/0.1% TFA. 0.5 $\mu$l of matrix solution, followed by 0.5 $\mu$l of peptide sample, is applied to analysis plate wells and allowed to dry. The analysis plate is loaded into the machine and the samples scanned and analyzed using a Reflector Delayed-Extraction method optimized for peptides. For each sample, a cumulative data signal from 32–128 laser shots is collected and analyzed. Each run includes a sample well with a standard peptide for calibration.

Specific Synthesis

Preparation of $(Lys(Alloc)^{12,12})$-hGRF(1-29)-$NH_2$

The $[Lys(Alloc)^{12,21}]$-hGRF(1-29)-PAL-PEG-PS-resin was initially assembled by Fmoc chemistry on the Applied Biosystems 431A peptide synthesizer (sec Synthesis Methods above), including deprotection of the N-terminal residue Fmoc group.

The peptide-resin was cleaved with a mixture of TFA:1, 2-ethanedithiol:thioanisole:water (10:0.5:0.5:0.5 (v/v)) for 2 hrs, and the peptide isolated by precipitation in MTBE to give 240 mg of crude peptide. Purification by preparative reverse-phase HPLC with a Vydac C18 column (22×250 mm) resulted in 60 mg of purified product (>95% by analytical HPLC). MALDI-TOF mass spec: Calculated: 3523.8, Observed: 3524.2.

Preparation of $(N^{\alpha}$-isopropyl-Tyr$^1$,Lys(Alloc)$^{12}$-hGRF(1-29)-$NH_2$ Assembly of Initial $(Lys(Alloc)^{12})$-hGRF(1-29)-PAL-PEG-PS-Resin $(Lys(Alloc)^{12})$-hGRF(1-29)-PAL-PEG-PS-resin was initially assembled by Fmoc chemistry on the Applied Biosystems 431A peptide synthesizer (sec Synthesis Methods above), including deprotection of the N-terminal residue Fmoc group.

$N^{\alpha}$-Isopropylation by Reductive Alkylation

The $N^{\alpha}$-isopropyl group was added by reductive alkylation of the peptide-resin using sodium cyanoborohydride and the corresponding ketone (acetone) as described by Hocart, et al., 1987. 880 mg peptide-resin (approx. 70 $\mu$mols) was swelled in 5 ml DCM for 30 mins, then 10 mmol (174 $\mu$l) acetone in 7 ml MeOH/1% HOAc added and the mixture swirled intermittently for 2 hrs at ambient temperature. 2 mmols (129 mg) sodium cyanoborohydride in 12 ml MeOH/1% HOAc was then added, the mixture swirled intermittently for 2 hrs, then allowed to sit overnight (15 hrs). Qualitative ninhydrin. monitoring indicated a completed reaction (no blue color). The peptide-resin was cleaved with a mixture of TFA:1,2-ethanedithiol: thioanisole: water (10:0.5:0.5:0.5 (v/v)) for 2 hrs, and the peptide isolated by precipitation in MTBE to give approx. 200 mg of crude peptide. Purification by preparative reverse-phase gradient HPLC with Water/Acetonitrile/0.1% TFA solvents on a Vydac C18 column (22×250 mm) resulted in 50 mg of pure product (>95% by analytical HPLC). MALDI-TOF mass spec: Calculated: 3481.9, Observed: 3481.8.

EXAMPLE 9

Pegylation of the Protected hGRF(1-29)

The hGRF derivatives prepared as described in Example 8 were conjugated with activated PEG as described in Examples 1 and 6.

The purification in this case involved only a separation from excess reagents and side-products, whereas there was no need to carry out the procedure described in Example 2 and 3.

References

Abuchowski A. et al., *J. Biol Chem.*, 252, 3571–3581, 1977a;

Abuchowski A. et al., *J. Biol Chem.*, 252, 3582–3586, 1977b;

Beauchamp C. O. et al., *Anal. Biochem.*, 131, 25–33, 1983;

Caliceti et al., *J. Bioactive Compatible Polymer*, 8, 41–50. 1993;

Campbell R. et al., *J. Peptide Res.*, 49, 527–537, 1997;

Chan W. C. et al., *J. Chem. Soc. Chem. Commun.*, p. 2209, 1995;

Clark R. et al., *J. Biol. Chem.*, 36, 21969–21977, 1996;

Delgado C. et al., *Biotechnology and Applied Biochemistry*, 12, 119–128, 1990;

D. Bourgin and F. Dick et al., *Peptides* 1996, Proceedings of the 24th European Peptide Symposium, Edinburgh, Scotland, 1997;

Felix A. M. et al., *Int. J Peptide Protein Res.*, 46, 253–264, 1995;

Fisch et al., *Genes and Development*, 3, 1989, 198–211;

Greene T. W. et al., *Protective Groups in Organic Synthesis*, John Wiley and Sons, Inc. Pub., pp.331–333, 1991;

Habeed A. S. F. A., *Anal Biochem.*, 14, 328–336, 1966.

Harris J. M., *Rev. Macromol. Chem. Phys.*, C25, pp. 325–73, 1985;

Hocart et al., *J. Med Chem.*, 30(4), 739–743, 1987;

Lu et al., *Int. J. Peptide Protein Res.* 43. 1994, 127–138;

Monfardini et al., *Biocon. Chem.*, 6, 62–69, 1995;

Morpurgo et al., *Biocon. Chem.*, 7, 363–368, 1996;

Murphy, W. A. et al., *Peptide Research*, 1(1), 36, 1988;

Pande C. S., et al., *Proc. Natl. Acad. Sci. USA*, 77, 895–899, 1980;

Sartore L., et al., *Appl. Biochem. Biotechnol.*, 27, 45, 1991;

Sartore L., et al., *Applied Biochem. Biotechnol.*, 31, 213–22, 1991;

Sims G. E. C. et al., *Anal. Biochem*, 107, 60–63, 1980;

Tam, J. P. et al., Strong and Deprotection of Synthetic Peptides: Mechanism and Methods, *The Peptides*, vol. 9, Academic Press Inc., 1997;

Veronese F. M., et al., i Appl Biochem., 11, 141–152 (1985);

Miyata et al., *Agric. Biol. Chem.*, 52, 1575–1581, 1988;

Zalipsky S. et al., *Polymeric Drugs and Drug Delivery Systems*, adrs 9-110 ACS Symposium series 469, 1990; and Zalipsky S. et al., *Europ. Polym. J.*, 19, 1177–1183, 1983.

---

---

What is claimed is:

1. A human growth hormone releasing factor-polyethylene glycol (hGRF-PEG) conjugate consisting of a human growth hormone releasing factor (hGRF) comprising the amino acid sequence of SEQ ID NO:1, wherein said hGRF has at least one polyethylene glycol (PEG) unit per hGRF covalently bound to only the amino acids selected from the group consisting of at least one amino group of $Lys^{12}$ of SEQ ID NO:1, $Lys^{21}$ of SEQ ID NO:1, and the amino terminal group ($N^{\alpha}$) of said hGRF, and wherein said hGRF-PEG conjugate does not contain a triazine group.

2. A human growth hormone releasing factor-polyethylene glycol (hGRF-PEG) conjugate according to claim 1, in which 1 PEG unit is covalently bound to the amino group of $Lys^{21}$ of SEQ ID NO:1.

3. A human growth hormone releasing factor-polyethylene glycol (hGRF-PEG) conjugate according to claim 1, in which 1 PEG unit is covalently bound to the amino group of each of $Lys^{12}$ and $Lys^{21}$ of SEQ ID NO:1.

4. A human growth hormone releasing factor-polyethylene glycol (hGRF-PEG) conjugate according to claim 1, in which 1 PEG unit is covalently bound group of each of $Lys^{12}$, $Lys^{21}$ and amino terminal group ($N^{\alpha}$) SEQ ID NO:1.

5. A pharmaceutical composition comprising a conjugate according to claim 1 in combination with a pharmaceutically acceptable carrier.

6. A human growth hormone releasing factor-polyethylene glycol (hGRF-PEG) conjugate according to claim 1, in which 1 PEG unit is covalently bound to the amino group of $Lys^{12}$ of SEQ ID NO:1.

7. A human growth hormone releasing factor-polyethylene glycol (hGRF-PEG) conjugate according to claim 1, wherein said hGRF has an amide group of the C-terminus.

8. A human growth hormone releasing factor-polyethylene glycol (hGRF-PEG) conjugate according to claim 1, wherein said hGRF consists of the amino acid sequence of SEQ ID NO:1, wherein said hGRF has at lest one polyethylene glycol (PEG) unit per hGRF covalently bound on only the amino acids selected from the group consisting of at least one of amine group of $Lys^{12}$ of SEQ ID NO:1, $Lys^{21}$ of SEQ ID NO:1, and the amino terminal group ($N^{\alpha}$) of said hGRF.

9. A human growth hormone releasing factor-polyethylene glycol (hGRF-PEG) conjugate according to claim 8, wherein said hGRF has an amide group at the C-terminus.

\* \* \* \* \*

UNITED STATES PATENT AND TRADEMARK OFFICE
CERTIFICATE OF CORRECTION

| | |
|---|---|
| PATENT NO. | : 6,528,485 B1 |
| APPLICATION NO. | : 09/587460 |
| DATED | : March 4, 2003 |
| INVENTOR(S) | : Veronese et al. |

Page 1 of 1

It is certified that error appears in the above-identified patent and that said Letters Patent is hereby corrected as shown below:

Column 20, line 52 (claim 4), after the word "bound" insert the phrase --to the amino--.

Column 20, line 53 (claim 4), after "($N^{\alpha}$)", insert the word --of--.

Signed and Sealed this

Tenth Day of June, 2008

JON W. DUDAS
*Director of the United States Patent and Trademark Office*

SEQUENCE LISTING

```
<160> NUMBER OF SEQ ID NOS: 1

<210> SEQ ID NO 1
<211> LENGTH: 29
<212> TYPE: PRT
<213> ORGANISM: Homo Sapiens
<220> FEATURE:
<221> NAME/KEY: MISC_FEATURE
<222> LOCATION: (29)..(29)
<223> OTHER INFORMATION: C-terminal Arg residue 29 may be amidated

<400> SEQUENCE: 1

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg
            20                  25
```